United States Patent
Günther et al.

(10) Patent No.: US 10,804,090 B2
(45) Date of Patent: *Oct. 13, 2020

(54) LASER ABLATION CELL

(71) Applicants: ETH ZÜRICH, Zürich (CH); Paul Scherrer Institut, Psi (CH)

(72) Inventors: Detlef Günther, Zürich (CH); Daniel Grolimund, Fulenbach (CH); Hao Wang, Zürich (CH)

(73) Assignees: ETH ZÜRICH, Zurich (CH); PAUL SCHERRER INSTITUT, Psi (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,859

(22) Filed: Apr. 25, 2019

(65) Prior Publication Data
US 2019/0355564 A1     Nov. 21, 2019

Related U.S. Application Data

(63) Continuation of application No. 15/336,361, filed on Oct. 27, 2016, now Pat. No. 10,319,576, which is a
(Continued)

(51) Int. Cl.
*H01J 49/10* (2006.01)
*G01N 33/68* (2006.01)
(Continued)

(52) U.S. Cl.
CPC ...... *H01J 49/105* (2013.01); *G01N 33/57415* (2013.01); *G01N 33/60* (2013.01);
(Continued)

(58) Field of Classification Search
CPC ........... H01J 49/105; H01J 49/10; H01J 49/02
(Continued)

(56) References Cited

U.S. PATENT DOCUMENTS 6,683,301 B2 * 1/2004 Whitehouse ........... B82Y 30/00
                                                          250/287
7,135,269 B2   11/2006 Hatakeyama et al.
(Continued)

FOREIGN PATENT DOCUMENTS

CN          2884188 Y        3/2007
DE     103 54 787 A1 *   6/2005   ............. G01N 27/62
(Continued)

OTHER PUBLICATIONS

DE 103 54 787 A1 Translation of Abstract and Description, obtained from espacenet on Mar. 17, 2020, pp. 1-23. (Year: 2020).*
(Continued)

*Primary Examiner* — Christine T Mui
(74) *Attorney, Agent, or Firm* — Kilpatrick Townsend & Stockton LLP

(57) ABSTRACT

A laser ablation cell (1) comprises a flow channel (11) having an essentially constant cross-sectional area so as to ensure a strictly laminar flow in the flow channel. A sample chamber (21) is provided adjacent to a lateral opening (14) of the flow channel. A laser beam (41) enters the sample chamber (21) through a lateral window (16) and impinges on a surface (24) of a sample (23) to ablate material from the sample. The sample may be positioned in such a distance from the flow channel that the laser-generated aerosol mass distribution has its center within the flow channel. This leads to short aerosol washout times. The laser ablation cell is particularly well suited for aerosol generation in inductively coupled plasma mass spectrometry (ICPMS), including imaging applications.

12 Claims, 7 Drawing Sheets

Related U.S. Application Data continuation of application No. 14/223,606, filed on Mar. 24, 2014, now Pat. No. 9,496,124, which is a continuation of application No. PCT/EP2013/056115, filed on Mar. 22, 2013.

(51) Int. Cl.
| | |
|---|---|
| *H01J 49/00* | (2006.01) |
| *H01J 49/40* | (2006.01) |
| *G01N 33/60* | (2006.01) |
| *G01N 33/574* | (2006.01) |
| *H01J 49/04* | (2006.01) |

(52) U.S. Cl.
CPC ...... *G01N 33/6848* (2013.01); *H01J 49/0004* (2013.01); *H01J 49/0031* (2013.01); *H01J 49/04* (2013.01); *H01J 49/0409* (2013.01); *H01J 49/0459* (2013.01); *H01J 49/0463* (2013.01); *H01J 49/40* (2013.01)

(58) Field of Classification Search
USPC ........................................ 250/287, 286, 281
See application file for complete search history.

(56) References Cited

U.S. PATENT DOCUMENTS

| | | |
|---|---|---|
| 7,135,296 B2 | 11/2006 | Baranov et al. |
| 7,479,630 B2 | 1/2009 | Bandura et al. |
| 7,893,408 B2 | 2/2011 | Hieftje et al. |
| 8,003,312 B2 | 8/2011 | Krutzik et al. |
| 8,034,609 B2 | 10/2011 | Hoh et al. |
| 9,496,124 B2 | 11/2016 | Gunther et al. |
| 2004/0175842 A1 | 9/2004 | Roitman et al. |
| 2005/0161598 A1 | 7/2005 | Guevremont et al. |
| 2005/0218319 A1 | 10/2005 | Bandura et al. |
| 2006/0278824 A1 | 12/2006 | Truche et al. |
| 2006/0289734 A1 | 12/2006 | Truche et al. |
| 2007/0042496 A1 | 2/2007 | Okamoto et al. |
| 2008/0017793 A1 | 1/2008 | James et al. |
| 2008/0128614 A1 | 6/2008 | Nikolaev et al. |
| 2008/0210857 A1 | 9/2008 | Felton et al. |
| 2009/0272893 A1 | 11/2009 | Hieftje et al. |
| 2009/0289184 A1 | 11/2009 | Deininger et al. |
| 2010/0012831 A1 | 1/2010 | Vertes et al. |
| 2010/0144056 A1 | 6/2010 | Winnik et al. |
| 2011/0042564 A1 | 2/2011 | Naito et al. |
| 2011/0280455 A1 | 11/2011 | Alexandrov |
| 2012/0016598 A1 | 1/2012 | Deininger et al. |
| 2012/0017183 A1 | 1/2012 | Ye et al. |
| 2012/0099103 A1 | 4/2012 | Hahn |
| 2012/0104244 A1 | 5/2012 | Verbeck, IV et al. |
| 2012/0178183 A1 | 7/2012 | Nolan et al. |
| 2012/0209854 A1 | 8/2012 | Ikegami |
| 2013/0056628 A1 | 3/2013 | Holle et al. |
| 2013/0162991 A1 | 6/2013 | O'Connor et al. |
| 2013/0289892 A1 | 10/2013 | Satoh |
| 2014/0102550 A1 | 4/2014 | Kline |
| 2014/0121117 A1 | 5/2014 | Tanner |
| 2014/0223991 A1 | 8/2014 | Hilliard et al. |
| 2014/0224775 A1 | 8/2014 | Sharp et al. |
| 2014/0227776 A1 | 8/2014 | Sharp et al. |
| 2014/0268134 A1 | 9/2014 | O'Connor |
| 2014/0287953 A1 | 9/2014 | Gunther et al. |
| 2015/0165550 A1 | 6/2015 | Fry et al. |
| 2015/0357173 A1 | 12/2015 | Koeppen et al. |
| 2016/0005578 A1 | 1/2016 | Koeppen et al. |
| 2016/0049283 A1 | 2/2016 | Gunther et al. |

FOREIGN PATENT DOCUMENTS

| | | | |
|---|---|---|---|
| FR | 2 883 977 A1 | 10/2006 | |
| JP | 11-201945 A2 | 7/1999 | |
| WO | 2009/0156725 A1 | 12/2009 | |
| WO | 2010/089611 A1 | 8/2010 | |
| WO | 2010/116961 A1 | 10/2010 | |
| WO | 2011/111852 A1 | 9/2011 | |
| WO | 2014/079802 A2 | 5/2014 | |
| WO | 2014/114803 A2 | 7/2014 | |
| WO | 2014/140627 A1 | 9/2014 | |
| WO | 2014/169394 A1 | 10/2014 | |

OTHER PUBLICATIONS

Arrowsmith et al., "Entrainment and Transport of Laser Ablated Plumes for Subsequent Elemental Analysis", Applied Spectroscopy, 1988, 42(7), 1231-1239.

Becker et al., "Imaging of Copper, Zinc, and Other Elements in Thin Section of Human Brain Samples (Hippocampus) by Laser Ablation Inductively Coupled Plasma Mass Spectrometry", Anal. Chem. 2005, 77, pp. 3208-3216.

Becker et al., "Bioimaging of metals in brain tissue by laser ablation inductively coupled plasma mass spectrometry (LA-ICP-MS) and metallomics", Metallomics, 2010, 2, pp. 104-111.

Becker et al., "Mass Spectrometry Imaging (MSI) of Metals in Mouse Spinal Cord by Laser Ablation ICP-MS", Metallonics, 2012, 4 284-288.

Bendall et al., "Single-Cell Mass Cytometry of Differential Immune and Drug Responses Across a Human Hematopoietic Continuum", Science, May 6, 2011, 332(6030), pp. 687-696.

Chery et al., "Detection of metals in proteins by means of polyacrylamide gel electrophoresis and laser ablation- inductively coupled plasma-mass spectrometry: Application to selenium", Electrophoresis, 2003, 24, pp. 3305-3313.

Drescher et al., "Quantitative Imaging of Gold and Silver Nanoparticles in Single.Eukaryotic Cells by Laser Ablation ICP-MS", Anal. Chem., 2012, 84, 9684-968.

Gao et al., "Single-Cell Elemental Analysis via High Irradiance Femtosecond Laser Ionization Time-of-Flight Mass Spectrometry", Anal. Chem. 2013, 85, pp. 4268-4272.

Giesen et al., "Multiplezed Immunohistochemical Detection of Tumor Markers in Breast Cancer Tissue Using Laser Ablation Inductively Coupled Plasma Mass Spectrometry", Anal. Chem. 2011, 83, pp. 8177-8133.

Giesen "ICP-MS and Elemental Tags for the Life Sciences", BAM-Dissertation,.Universitat zu Berlin, 2012, 199 pages.

Gurevich et al, A simple laser ICP-MS ablation cell with wash-out time less than 100 ms, J. Anal. At. Spectrom., 2007, 22, 1043-1050. (Year: 2007).

Hu et al., "Detection of Multiple Proteins on One Spot by Laser Ablation Inductively Coupled Plasma Mass Spectrometry and Application to Immuno-Microarray with Element-Tagged Antibodies", Anal. Chem., 2007, 79, pp. 923-929.

Hutchinson et al., "Imaging and spatial distribution of B-amyloid peptide and metal ions in Alzheimer's plaques by laser ablation-inductively coupled plasma-mass spectrometry", Anal. Biochem, 2005, 346, pp. 225-233.

Jeol, Laser Ablation Apparatus, English Machine Translation of JP H 11-201945 A, obtained on Mar. 8, 2017, pp. -10.(Year: 1999).

Koch et al., "Review of the State-of-the-Art of Laser Ablation Inductively Coupled Plasma Mass Spectrometry", Applied Spectroscopy, Feb. 4, 2011, pp. 155A-162A.

Konz et al., "Laser Ablation ICP-MS for Quantitative Biomedical Applications", Anal Bioanal Chem, 2012, 403, 2113-2125.

Lanni et al., "Mass spectrometry imaging and profiling of single cells", J. Proteomics, Aug. 30, 2012, 75, pp. 5036-5051.

Leach et al., "Standardless Semiquantitative Analysis of Metals Using Single-Shot Laser Ablation Inductively Coupled Plasma Time-of-Flight Mass Spectrometry", Anal. Chem., 2001, 73, pgs. pp. 2959-2967.

Leach et al., "Factors Affecting the Production of Fast Transient Signals in Single Shot Laser Ablation Inductively Coupled Plasma Mass Spectrometry", Appl. Spectroscopy., 2002, vol. 56, No. 1, pp. 62-69.

Leach et al., "Identification of alloys using single shot laser ablation inductively coupled plasma time-of-flight mass spectrometry", J. Anal. At. Spectrom., 2002, 17, pp. 852-857.

(56) References Cited

OTHER PUBLICATIONS

Managh et al., "Single Cell Tracking of Gadolinium Labeled CD4+ T Cells by Laser Ablation Inductively Coupled Plasma Mass Spectrometry", Anal. Chem., 2013, 85, pp. 10627-10634.

Matusch et al., "Cerebral Bioimaging of Cu, Fe, Zn, and Mn in the MPTP Mouse Model of Parkinson's Disease Using Laser Ablation Inductively Coupled Plasma Mass Spectrometry (LA-ICP-MS)", J. Am. Soc. Mass. Spectrum, 2010, 21, 161-171.

Matusch et al., "Element imaging in formalin fixed slices of human mesencephalon", Int. J. Mass Spectrometry, 2011, 307, pp. 240-244.

Pisonero et al., "High Efficiency Aerosol Dispersion Cell for Laser Ablation-ICP-MS," Journal Analyt Atomic Spect, 2006, vol. 21, No. 9, p. 922.

Seuma et al., "Combination of immunohistochemistry and laser ablation ICP mass spectrometry for imaging of cancer biomarkers", Proteomics, 2008, 8, pp. 3775-3784.

Shrestha et al., "In Situ Metabolic Profiling of Single Cells by Laser Ablation Electrospray Ionization Mass Spectrometry", Anal. Chem., 2009, 81, pp. 8265-8271.

Waentig et al., "Multi-parametric analysis of cytochrome P450 expression in rat liver microsomes by LA-ICP-MS", J. Anal. At. Spectrom., 2011, pp. 26, pp. 310-319.

Wang et al., "ICP-MS-Based Strategies for Protein Quantification", Mass Spectrometry Reviews, 2010, 29, pp. 326-348.

Wang et al, "High Spatial Resolution Chemical Imaging by Laser Ablation Inductively Coupled Plasma Mass Spectrometry (LA-ICPMS) using a Novel Fast Washout Ablation Cell: A Comparison with Synchrotron Micro/Nano X-ray Fluorescence (SR-Micro/NanoXRF", Abstract on 11th European Workshop on Laser Ablation, 2012, 19-22.

Zhang et al., "A novel combination of immunoreaction and ICP-MS as a hyphenated technique for the determination of thyroid-stimulating hormone (TSH) in human serum", The Royal Society of Chemistry, 2001, 16, pp. 1393-1396.

\* cited by examiner (a)

(b)

(c)

(a)

(b)

(a) 
(b) 
(c) 
(d)

— 20μm

LASER ABLATION CELL

REFERENCE TO RELATED APPLICATIONS

This application is a continuation of U.S. patent application Ser. No. 15/336,361, filed on Oct. 27, 2016; which is a continuation of U.S. patent application Ser. No. 14/223,606, filed on Mar. 24, 2014, now U.S. Pat. No. 9,496,124; which is a continuation of International PCT Application No. PCT/EP2013/056115, filed Mar. 22, 2013, the entire contents of which are hereby incorporated herein by reference.

TECHNICAL FIELD

The present invention relates to a laser ablation cell, to an ablation apparatus and an inductively coupled plasma (ICP) ion source employing such a laser ablation cell, and to a method of using such a laser ablation cell, for example for the imaging of biological material.

BACKGROUND

Inductively coupled plasma mass spectrometry (ICPMS) provides accurate quantitative information on major, minor, trace, and ultra-trace elements of industrial, geological, environmental, and biological samples. In ICPMS, an aerosol sample is carried by a carrier gas stream to a so-called ICP torch. In this torch, the gas is subjected to intense high-frequency electromagnetic fields, which lead to the formation of a plasma by induction. The ions from the plasma are then extracted into a mass spectrometer, where they are separated on the basis of their mass-to-charge ratios.

ICPMS can be coupled with laser ablation (LA) to ablate material from a solid sample so as to create the aerosol required for ICP. Ablation may be carried out directly in the ICP torch, or the sample may be placed in an external laser ablation cell upstream of the ICP torch, and the aerosol created by laser ablation is transported to the ICP torch by the carrier gas stream. For example, reference 1 demonstrated a laser ablation cell (the so-called HEAD cell) for which the aerosol ejection direction is parallel to that of the carrier gas. Another laser ablation cell design based on a similar principle is demonstrated in reference 2.

Since the first half of 1990s, attempts have been made to use laser-ablation ICPMS (LA-ICPMS) as a chemical imaging tool by scanning the laser spot over the sample surface. Many studies have demonstrated the potential imaging capabilities of LA-ICPMS based on a considerable variety of hard and soft samples. Most of these studies showed an effective spatial resolution of approximately 5-100 μm. Although LA-ICP-MS offers highly multiplexed quantitative analysis of antigen expression in single cells, it currently lacks the resolution necessary for the imaging of single cells within tissue samples.

However, some applications, such as diagnostic analysis of tissue sections, requires higher spatial resolution, e.g. to visualize cell-to-cell variability. The effective spatial resolution is determined by the laser spot size convoluted with the system dispersion. The system dispersion is in turn often dominated by a compromise between the aerosol washout time after each laser shot and the scanning speed. The longer the washout time, the more overlap will occur between signals originating from neighboring sample spots if the scanning speed is kept fixed. Therefore, aerosol washout time often is one of the key limiting factors for improving resolution without increasing total scan time.

The fastest washout time can be achieved by in-torch ablation, resulting in single shot signal durations of a few milliseconds. However, in-torch ablation is limited to very small samples, and scanning of the laser spot is very difficult to realize with in-torch ablation. Therefore, for imaging applications, external laser ablation cells are generally employed. However, even with the best known cell designs, washout times are often on the scale of seconds, and short washout times under 100 milliseconds are hard to achieve.

It is an object of the invention to provide further and improved laser ablation cells, ablation apparatus incorporating such cells (for example, linked to an ICP-MS), which have an application in techniques for imaging of biological material, such as tissue samples, monolayers of cells and biofilms, and in particular to adapt LA-ICP-MS for use as a single-cell imaging technique.

SUMMARY OF THE INVENTION

In a first aspect, the present invention provides a laser ablation cell that has the potential of achieving short aerosol washout times.

Accordingly, a laser ablation cell is provided, comprising a flow channel having an inlet for feeding a carrier gas to the flow channel and having an outlet. A lateral opening is provided in a first wall portion of the flow channel, and a lateral window is disposed in a second wall portion of the flow channel opposite of the lateral opening. A sample chamber is provided adjacent to the lateral opening. The sample chamber is configured to receive a sample in a manner to enable a laser beam to enter the sample chamber through the lateral window and the lateral opening and to impinge on a surface of the sample, so as to ablate material from the sample surface and to create an aerosol. The sample chamber has an inlet for feeding a sheath gas to the sample chamber.

The inlet and outlet of the flow channel may be connected to tubing having essentially the same cross-sectional area as the flow channel itself. In this manner, the flow channel essentially acts like a single piece of tubing. The ablation cell of the present invention may therefore be considered to have a "tube cell" design. By minimizing variations of the cross-sectional area (and preferably also of the cross-sectional shape) of the flow channel, this "tube cell" design allows maintaining an essentially laminar flow pattern in the flow channel, avoiding turbulences as far as possible. Furthermore, the design allows positioning the sample sufficiently close to the flow channel that a major proportion of the laser-induced aerosol plume is introduced directly into the flow of the carrier gas. These measures significantly reduce dispersion. In practice, the present cell design allows reducing the washout time to below 30 ms (full width at 1% maximum) and minimizing the tailing of the sample washout. This improvement is observed for elements across the entire atomic mass range. Thus the invention provides a tube cell laser ablation cell. The invention also provides an ablation cell with a wash out time of less than 90 ms, for example less than 30 ms.

The flow channel preferably has a cross-sectional area that is essentially constant or at most varies weakly. In particular, preferably the cross-sectional area of the flow channel is essentially constant in the vicinity of the lateral opening. The cross-sectional area of the flow channel may be regarded to vary at most weakly if any variations in cross section do not significantly disturb laminar flow. In particular, the cross-sectional area may be considered to vary at most weakly if the variation of the average diameter of the flow channel is less than 1.5 mm per 1 mm length along the tube axis, preferably less than 0.5 mm per 1 mm length along the tube axis, more preferably less than 0.2 mm per 1 mm length along the tube axis for any cross-sectional plane along the flow channel. It is preferred that the flow channel does not form a pronounced constriction at the lateral opening so as to avoid pronounced suction effects, as in a Venturi tube, and that the flow channel does not widen up significantly in the vicinity of the lateral opening so as to avoid that the carrier gas is pushed into the sample chamber by the resulting positive pressure difference.

In absolute numbers, the cross-sectional area may take a wide range of values, depending on laser spot size and laser energy. The mean diameter of the flow channel (calculated as $d=2\sqrt{A/\pi}$, where A is the cross-sectional area) may range, e.g., from 50 micrometers to 5 millimeters, preferably from 200 micrometers to 5 millimeters.

The angle between the inlet and the outlet of the flow channel is preferably at least 160° (to be precise, between 160° and 200°), more preferably at least 170° (to be precise, between 170° and 190°). In other words, the flow channel is preferably essentially straight or bent by not more than 20° or better not more than 10° in any direction. An arbitrary direction of the sheath gas inlet relative to the direction of the flow channel may be chosen. Preferably, the sheath gas inlet extends perpendicular to the transversal direction.

The flow channel and the sample chamber are separated by a separating wall, which forms the first wall portion of the flow channel in which the lateral opening is arranged. In order to allow the sample to be positioned sufficiently close to the flow channel, the separating wall preferably has a minimum thickness of less than 500 micrometers, more preferably less than 200 micrometers. It should be noted that the thickness of the separating wall may vary along the circumference of the flow channel; the separating wall will normally have its smallest thickness immediately adjacent to the opening between the tube and the sample chamber, and the thickness will increase away from the opening in a plane perpendicular to the tube axis. The thickness may further vary along the length of the flow channel.

In order to minimize flow disturbances induced by the lateral opening, the cross-sectional area of this opening should be kept small. On the other hand, it may be desirable to make the opening sufficiently large to enable the laser beam to be scanned over the sample surface without moving the sample relative to the opening. As a compromise, the cross-sectional area of the lateral opening is preferably not more than about 20 mm², more preferably not more than about 7 mm². Expressed relative to the cross-sectional area of the flow channel, the ratio of the cross-sectional areas of the opening and the flow channel is preferably not more than about 5, more preferably not more than about 3, most preferably not more than about 1. In order to enable a laser beam to pass through the lateral opening, the lateral opening should preferably have a cross-sectional area of at least about 0.01 mm². The width of the lateral opening transverse to the flow channel is preferably less than 80% of the mean diameter of the flow channel, and more preferably less than 50% of the mean diameter of the flow channel. The length of the lateral opening in the direction of the flow channel is preferably not more than five times the mean diameter of the flow channel and more preferably not more than three times or even 1.5 times the diameter of the flow channel.

In order to enable easy sample exchange, the laser ablation cell preferably has a two-part design, comprising a first cell part (in the following referred to as a "cell top") that houses the flow channel and a second cell part (in the following referred to as a "cell bottom") that forms the sample chamber. The cell bottom is preferably removable from the cell top for exchanging the sample. The cell bottom is preferably open towards the cell top, i.e., the separating wall between the sample chamber and the flow channel is preferably formed by the cell top rather than by the cell bottom. The terms "top" and "bottom" are to be understood as not defining an absolute orientation of these parts; these terms are only used to better distinguish between the different cell parts, and the laser ablation cell may as well be used in an inverted orientation where the cell top is pointing towards the floor and the cell bottom is pointing towards the ceiling.

The invention further relates to a complete ablation apparatus comprising an ablation cell as described above. The ablation apparatus further comprises a laser, in particular, a UV laser, for shooting a laser beam through the lateral window and the lateral opening and onto the sample surface, and a positioning device for changing the relative position between the sample and the laser beam. The positioning device may comprise, e.g., any of the following: an x-y or x-y-z stage for moving the entire laser ablation cell relative to the laser; an x-y or x-y-z stage for moving the sample within the laser ablation cell while keeping the relative position between the ablation cell and the laser fixed; a beam deflector for deflecting the laser beam while keeping the relative position between the ablation cell and the laser fixed; etc. The positioning device may be employed to scan the laser beam over the sample surface. The resulting aerosol may subsequently be analyzed with respect to its elemental or isotopic composition, e.g., by ICPMS. In this manner, the sample surface may be imaged according to its elemental or isotopic composition. However, the present invention is not limited to the use of the ablation cell in conjunction with ICPMS imaging and may also be employed in other methods in which short aerosol pulses are required.

The invention further provides an ICP ion source comprising an ablation cell as described above. The ICP source further comprises an ICP torch connected to the outlet of the ablation cell, and tubing connecting said ablation cell to the ICP torch. Preferably the tubing has a cross-sectional area that is essentially identical to the cross-sectional area of the flow channel of the ablation cell or changes only weakly as compared to the cross-sectional area of the flow channel, so as to maintain a laminar flow with minimum dispersion over the entire length of the tubing.

The invention also encompasses an ICPMS system comprising such an ICP ion source and a mass analyzer coupled to the ion source. The mass analyzer may, e.g., be a quadrupole mass analyzer, a time-of-flight (TOF) mass analyzer, or a sector field mass analyzer, in particular, a Mattauch-Herzog mass analyzer. However, the invention is not restricted to any particular type of mass analyzer.

The invention further provides a method of operating an ablation cell as described above. The method comprises, not necessarily in the given order:

placing a sample in the sample chamber such that a surface of the sample faces the lateral opening;

feeding a carrier gas to the inlet of the flow channel;

feeding a sheath gas to the inlet of the sample chamber; and ablating material from the surface by shooting a pulsed laser beam through the lateral window and the lateral opening and onto said surface.

The direction of the laser beam, the orientation of the lateral window and the lateral opening, and consequently the orientation of the sample may be arbitrary in space. For instance, the laser beam may be directed upwards, downwards, sideway etc., and the sample surface may be oriented in any orientation that allows the laser beam to reach the sample surface.

Each laser pulse will cause a quasi-instantaneous laser-generated aerosol mass distribution ("plume"). Here, "quasi-instantaneous" means a time scale that is much shorter than the time scale of mass transport by the carrier gas stream and the sheath gas stream. The laser-generated aerosol mass distribution is caused by the action of the laser pulse alone, neglecting the normal gas flow of the carrier and sheath gases. This mass distribution is established within less than 1 millisecond after the first interaction of the laser pulse with the sample. The sample is preferably positioned at such a distance from the flow channel that the quasi-instantaneous laser-generated aerosol mass distribution has its center within the flow channel, between the lateral opening and the lateral window. The center of the mass distribution is defined in the usual manner, in the same way as the center-of-mass of a rigid body, integrating over the entire aerosol plume. In this manner, the majority of the aerosol plume is directly injected into the stream of the carrier gas and may be transported away by the stream of the carrier gas with minimum dispersion.

The optimum distance between the sample surface and the center axis of the flow channel will depend on the type of laser, the energy of the laser beam, the type of carrier and sheath gases, and the flow rates of the gases. For instance, for a standard ArF excimer laser with pulses in the nanosecond range, argon as carrier gas at a flow rate of 1.1 L/min, and helium as sheath gas at a flow rate of 0.6 L/min, a distance of about 2 has turned out to be optimal. In more general terms, the sample should preferably be positioned in such a manner that the surface of the sample has a distance from the center axis of the flow channel in the range of 0.5 millimeters to 4.5 millimeters for laser pulses in the range of 50 femtoseconds to 50 nanoseconds.

In consequence, the optimum distance between the sample surface and the separating wall that separates the sample chamber from the flow channel will depend on various parameters. This distance may range from less than 50 micrometers to 1 millimeter or more. The distance should be large enough to allow the sheath gas to flow along the surface of the sample and through the lateral opening into the flow channel.

The sheath gas fulfills at least three tasks: it flushes the aerosol in axis with the aerosol injection direction, which helps the uptake of the aerosol particles in the carrier gas stream; it forms a "protection region" above the sample surface and ensures that the ablation is carried out under a controlled atmosphere; and it increases the flow speed in the flow channel. Preferably the viscosity of the sheath gas is lower than the viscosity of the primary carrier gas. This helps to confine the aerosol in the center of the flow channel and to minimize the aerosol dispersion downstream from the ablation cell. In particular, the carrier gas is preferably argon (Ar). Argon is particularly well-suited for stopping the aerosol expansion before it reaches the walls of the flow channel, and it is also required for an improved instrumental sensitivity in most of the Ar gas based ICP. The sheath gas is preferably helium (He). However, the sheath gas may be replaced by or contain other gases, e.g., hydrogen, nitrogen, or water vapor. Preferably the main proportion of the sheath gas is helium, e.g., at least 50% by volume. At 25° C., Ar has a viscosity of 22.6 μPas, whereas He has a viscosity of 19.8 μPas.

The optimum flow rates of the carrier gas and the sheath gas will depend on a variety of factors, first of all on geometry, in particular, on the cross-sectional area of the flow channel. Secondly, they will depend on the geometry of the lateral opening. However, it is preferred that the volume flow rate of the sheath gas is smaller than the volume flow rate of the carrier gas, in particular, 0.3 to 1.0 times the volume flow rate of the carrier gas. The flow rate of the sheath gas may be adjusted to help to inject the center of the aerosol plume close to the center of the flow channel.

The method of the present invention is particularly suited for chemical imaging. To this end, the above method may comprise scanning the laser beam over the surface and analyzing the resulting aerosol to obtain a chemical image of the sample surface. Analysis may be carried out by mass spectrometry, in particular, by ICPMS, but may also be carried out by any other suitable method.

The method is well suited for the investigation of biological samples, in particular, of tissue samples of human or animal tissue. However, the method is not limited to biological samples and may as well be applied to other kinds of samples. When performed on biological samples, the method of the invention may be performed at a subcellular level, at a cellular level, or at lower resolution, wherein individual cells within a tissue are not individually resolved. In certain embodiments, the method of the invention uses the specific laser ablation cell disclosed herein. Thus the invention provides the use of an ablation cell with a wash out time of less than 100 ms for analysing biological samples.

The invention therefore also provides a method of imaging biological samples, such as a tissue sample, comprising (i) labelling at least one of a plurality of different target molecules in the tissue sample with at least one different labelling atom to provide a labelled tissue sample, wherein the labels can be distinguished by LA-ICP-MS to identify each of the at least one different target molecules, (ii) subjecting multiple cells of the labelled biological sample to laser ablation at multiple known locations, to form a plurality of plumes; and (iii) subjecting plumes to inductively coupled plasma mass spectrometry, whereby detection of labelling atoms in the plumes permits construction of an image of the biological sample.

In some embodiments, the at least one of a plurality of different target molecules is labelled with at least one different specific labelling construct (e.g. an antibody or nucleic acid or the like that binds specifically to the target molecule), wherein each different labelling construct is attached to a lanthanide labelling atom, and the laser ablation is at a resolution of the cellular level or better.

In some embodiments, each of the at least one of a plurality of different target molecules is labelled with at least one different specific labelling constructs, wherein each different labelling construct is attached to a lanthanide labelling atom, and the laser ablation is performed with a laser spot size of 25 μm or less.

In some embodiments, at least three different target molecules are labelled with at least three different labelling atoms, and the laser ablation is at a resolution of the cellular level or better.

In some embodiments, at least three different target molecules are labelled with at least three different labelling atoms, and the laser ablation is performed with a laser spot size of 25 μm or less.

In some embodiments, the at least one of a plurality of different target molecules is labelled with at least one different labelling atom, and the laser ablation is at a resolution of the sub-cellular level.

In some embodiments, the at least one of a plurality of different target molecules is labelled with at least one different labelling atom, and the laser ablation is performed with a laser spot size of 4 µm or less.

In some embodiments, the at least one of a plurality of different target molecules is labelled with at least one different labelling atom, and the inductively coupled plasma mass spectrometry uses a time-of-flight detector.

The invention also provides methods in which the analysis of biological samples is a step in methods of diagnosis, treatment, or monitoring of patients suffering from a disease.

These methods can use the ablation cell, ablation apparatus, ICP ion source or system as disclosed herein.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Laser Ablation Cell

Figure 1:
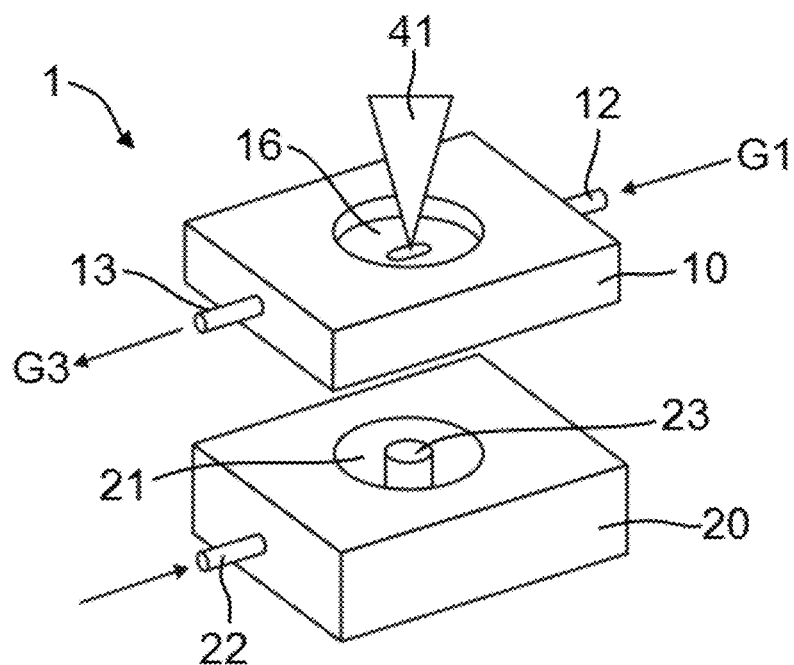
FIG. 1 shows a schematic sketch (not to scale) of a laser ablation cell according to the present invention in perspective view.
Figure 2:
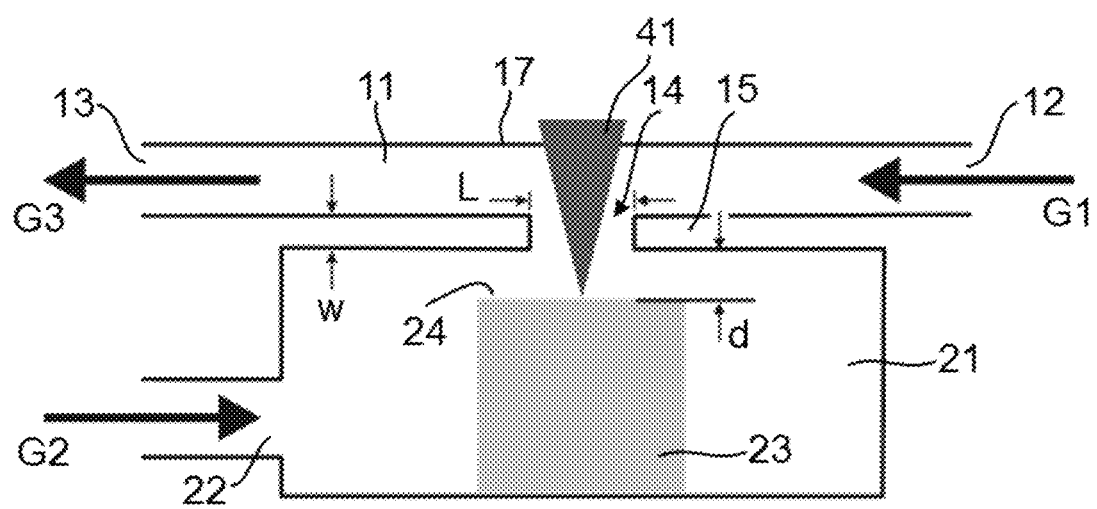
FIG. 2 shows a schematic sketch (not to scale) of the laser ablation cell of FIG. 1 in a central longitudinal section.

FIGS. 1 and 2 illustrate, in a schematic manner, a laser ablation cell 1, in the following also called a "tube cell", according to an exemplary embodiment of the present invention. The ablation cell 1 comprises two parts: a first part or cell top 10 and a second part or cell bottom 20. A tubular flow channel 11 is formed in the cell top 10 and extends from a carrier gas inlet 12 to a mixed-gas outlet 13. In a bottom wall portion 15 of the cell top 10, a lateral opening 14 is formed. In a top wall portion 17 of the cell top 10, a transversal hole is formed and closed by an UV transparent silicon window 16. In the cell bottom 20, a sample chamber 21 is provided. A sheath gas inlet 22 leads to the sample chamber 21. Whereas the sheath gas inlet 22 is shown as extending (anti-)parallel to the flow channel 11, an arbitrary direction of the sheath gas inlet may be chosen. Preferably, the sheath gas inlet extends perpendicular to the transversal direction. A sample 23 is placed in the sample chamber 21, and the cell bottom 20 is mounted to the cell top 10 such that the top surface 24 of the sample 23 is situated below the lateral opening 14.

For operating the ablation cell, a carrier gas G1 is fed to the inlet 12 of the flow channel 11, and a sheath gas G2 is fed to the inlet 22 of the sample chamber 21. A UV laser beam 41 enters the window 16, traverses the flow channel 11, exits the flow channel 11 through the lateral opening 14 and impinges on the top surface 24 of the sample 23.

Figure 3:
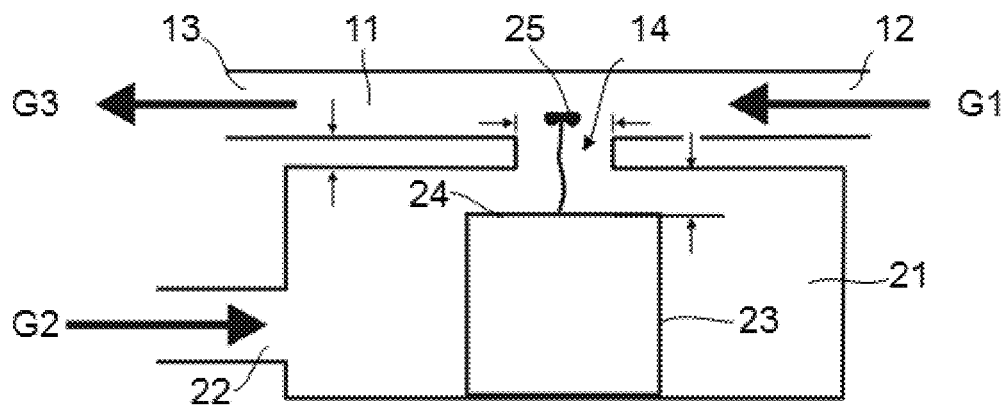
FIG. 3 shows a schematic illustration (not to scale) of the laser-generated plume in the laser ablation cell.

Each laser pulse generates an aerosol plume 25, as schematically illustrated in FIG. 3. This plume is the direct result of the action of the laser pulse; the initial mass distribution in the plume immediately after the end of the laser pulse is influenced only very little by the streams of the carrier gas G1 and the sheath gas G2. The design of the laser ablation cell 1 allows placing the center of the laser-generated aerosol mass distribution right in the flow channel, without the need of first transporting the aerosol to the flow channel by the sheath gas stream. The carrier gas G1 and sheath gas G2 then carry away the aerosol towards the outlet 13, where they exit the ablation cell as a mixed-gas stream G3.

As the carrier gas G1, argon (Ar) is preferred. As the sheath gas, preferably helium (He) is chosen. Ar is beneficial for stopping the aerosol expansion typically occurring in pure He atmospheres. Adding He from the sample container has three advantages: a) this setup flushes the aerosol in axis with the aerosol injection direction, which helps the uptake of the particles; b) He gas forms a 'protection' region above the sample surface and assures that the ablation is conducted under He atmosphere; c) mixing Ar and He already in the tube cell not only avoids the need of a dispersive gas adapter (Ar/He mixing bulb), but also increases the flow speed and gas viscosity comparing to normal setup using only He as carrier gas, hence decreases the aerosol dispersion.

Figure 4:
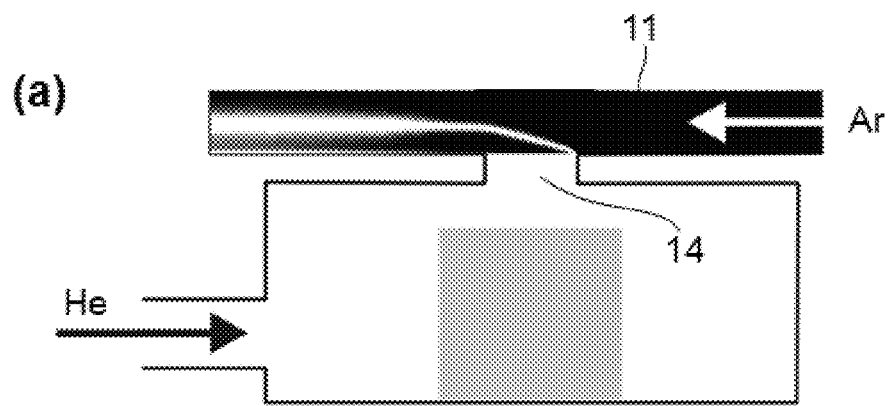
FIG. 4 illustrates, in a schematic manner, simulation results for the gas flow in the flow channel of the laser ablation cell; part (a) shows the mixing distribution pattern between He and Ar, where the ablated aerosol is located at the mixing interface above the lateral opening, the degree of mixing being indicated in gray scale, white representing the highest degree of mixture; part (b) shows the simulated gas flow velocity pattern, flow velocity being indicated in gray scale, white representing the highest flow velocity.
Figure 4:
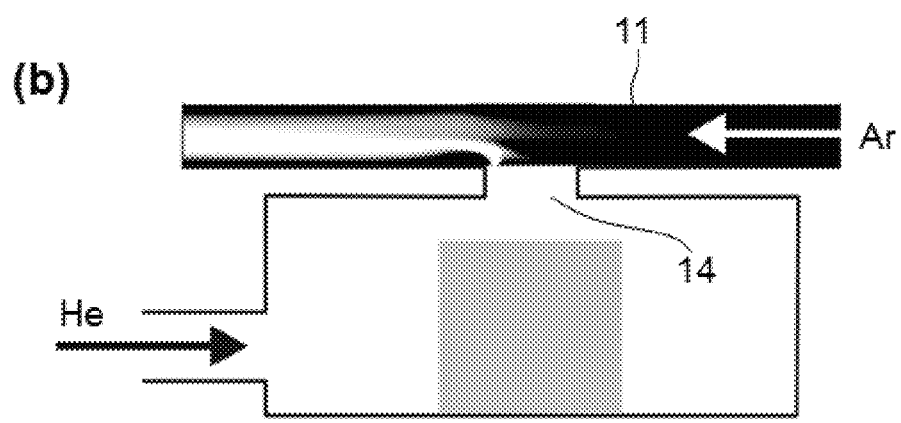

FIG. 4 shows results of computational fluid dynamics simulations carried out using the ANSYS CFX 12 software package (ANSYS Inc., Berlin, Germany). A shear stress transport model for turbulence was considered in the simulation. Simulations were carried out for the following parameters: Length of the lateral opening: L=4.5 mm; width of the lateral opening: 1.5 mm; minimum thickness of the bottom wall portion: w=50 micrometers; total length of the flow channel: 50 mm; diameter of the cylindrical sample chamber: 23 mm; distance between the top surface 24 of the sample 23 and the bottom wall portion 15: d=350 micrometers. Ar flow at the inlet was set to a constant speed of 2.6 m/s (1.1 L/min), while He was simulated using 1.4 m/s (0.6 L/min).

The mixture distribution of the two inlet gases is shown in FIG. 4(*a*). The mixing of the two gases is indicated in gray scale, white being the highest degree of mixture. A sharp interface at the lateral opening 14 is formed by the He flow entering into the Ar flow. Helium significantly dominates the opening region and forms together with Argon a boundary layer. Due to the least degree of mixing of the two gases at the lateral opening 14, and the previous results indicating that laser ablated aerosol penetrates easily in He but not in Ar, it can be assumed that the aerosol is not diffusing into the Argon atmosphere, is therefore not reaching the entire cross section of the flow channel, and remains very dense. The initially very sharp interface widens within a few millimeters downstream from the opening. By varying the combination of the inlet gas flows, the height of the boundary layer and accordingly the height of the ablated aerosol can be controlled.

The simulated gas flow speed distribution is shown in FIG. 4(*b*). The Ar inlet flow upstream of the lateral opening 14 represents a typical laminar flow distribution in the flow channel, being the fastest flow in the center of the tube, and decreasing gradually towards the tube wall. Simulating the emergence of the two gases showed no significant turbulence flow. Nevertheless, the calculated Reynolds number (~2000) is close to the transition from laminar to turbulent flow (2300~4000). However, using a turbulent model indicated a stringent laminar flow. Therefore it can be concluded that due to the absence of turbulences, a defined stopping distance for the laser aerosol close to the center of the tube cell which is matching the highest gas velocity, low aerosol dispersion should be achieved.

Figure 5:
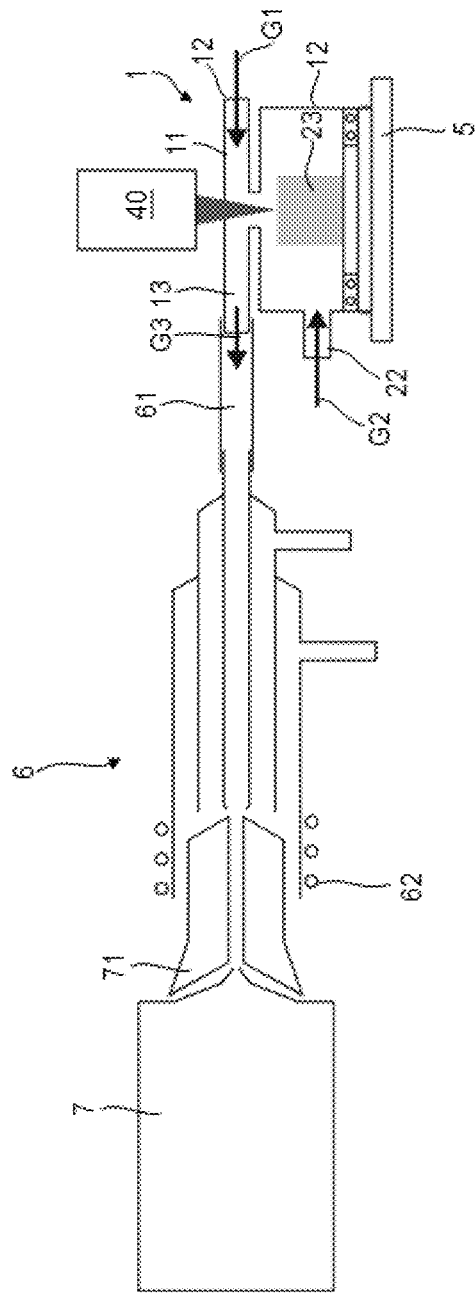
FIG. 5 illustrates, in a highly schematic manner, a complete LA-ICPMS system employing the laser ablation cell of FIG. 1.

FIG. 5 schematically illustrates a complete LA-ICPMS system. The laser beam is generated by a laser 40. The laser ablation cell 1 is mounted on an X-Y-Z stage 5 so as to be able to change the position of the sample relative to the laser beam. The outlet 13 of the laser ablation cell 1 is connected to an ICP torch 6 by tubing 61. The tubing 61 has essentially the same inner diameter as the flow channel 11 of the laser ablation cell 1 so as to ensure laminar flow of the outlet gas G3. The ICP torch generates a plasma source by operation of an RF coil 62; it is constructed in the usual manner ICP torches are well known in the art and do not require further explanations. The ICP torch is connected to a mass analyzer 7 via an ICP source 71. The mass analyzer may be a quadrupole mass analyzer, a time-of-flight (TOF) mass analyzer, a sector mass analyzer etc.

Of course, many modifications of the laser ablation cell and the LA-ICPMS setup are possible without leaving the scope of the present invention. In particular, the present invention is not limited to a particular choice of materials for the laser ablation cell, to a particular geometry or size of the sample chamber, to a particular geometry, length, and diameter of the flow channel in the ablation cell, to a particular geometry and size of the lateral opening in the ablation cell, to a particular window size or material, to a particular type of laser for ablation, to particular gas types introduced into the ablation cell, etc.

LA-ICP-MS Applications

ICP-MS has been used for single-cell analysis, but only for cells in suspension [3]. Laser ablation (LA) coupled to ICP-MS has now been adapted so that this technique is suitable for single-cell imaging in biological samples, such as in tissue samples. Although tissue imaging via LA-ICP-MS has previously been reported, the disclosed procedures have not achieved high spatial resolution. For instance, LA-ICP-MS has been used to obtain images of brain sections [4] and of cancer tissue [5, 6] but single-cell or subcellular resolution was not achieved. In all cases the resolution was limited by the spot size of the ablating laser and/or by overlap/mixing between the analysis of material released in consecutive ablations. For instance, a spot size of 40 μm [4] cannot ablate material with a resolution which is high enough for single-cell imaging in a tissue sample. Similarly, ablation at a frequency of 10 Hz will lead to overlapping signals if the ablated material cannot be transported to the ICP-MS in less than 100 ms; for example the ablation cell used in reference 5 with this ablation frequency had a washout time well in excess of 1 s (which the authors did not note).

An LA-ICP-MS system, which overcomes these drawbacks and is able to achieve sub-cellular resolution, is provided herein, thereby making available for the first time LA-ICP-MS techniques suitable for single-cell imaging of biological samples such as tissues. These techniques include the methods described below.

The invention therefore provides a method of imaging a biological sample, such as a tissue sample, comprising labelling at least one of a plurality of different target molecules in the biological sample with at least one different labelling atom, wherein each target is now labelled in a fashion it can be specifically identified, to provide a labelled biological sample, subjecting multiple cells of the labelled biological sample to laser ablation at multiple known locations, to form a plurality of plumes; and subjecting plumes to inductively coupled plasma mass spectrometry, whereby detection of labelling atoms in the plumes permits construction of an image of the biological sample.

In some embodiments, the at least one of a plurality of different target molecules is labelled with at least one different specific labelling construct (e.g. an antibody or nucleic acid or the like that binds specifically to the target molecule), wherein each different labelling construct is attached to a lanthanide labelling atom, and the laser ablation is at a resolution of the cellular level or better.

In some embodiments, the at least one of a plurality of different target molecules is labelled with at least one different specific labelling constructs, wherein each different labelling construct is attached to a lanthanide labelling atom, and the laser ablation is performed with a laser spot size of 25 μm or less.

In some embodiments, at least three different target molecules are labelled with at least three different labelling atoms, and the laser ablation is at a resolution of the cellular level or better.

In some embodiments, at least three different target molecules are labelled with at least three different labelling atoms, and the laser ablation is performed with a laser spot size of 25 μm or less.

In some embodiments, the at least one of a plurality of different target molecules is labelled with at least one different labelling atom, and the laser ablation is at a resolution of the sub-cellular level.

In some embodiments, the at least one of a plurality of different target molecules is labelled with at least one different labelling atom, and the laser ablation is performed with a laser spot size of 4 μm or less.

In some embodiments, the at least one of a plurality of different target molecules is labelled with at least one different labelling atom, and the inductively coupled plasma mass spectrometry uses a time-of-flight detector.

The invention also provides methods in which the analysis of biological samples is a step in methods of diagnosis, treatment, or monitoring of patients suffering from a disease.

These methods can use the ablation cell, ablation apparatus, ICP ion source or system as disclosed herein.

The invention also provides a method of labelling a biological sample with four or more (e.g. 5, 6, 7, 8, 9, 10, 12, 13, 14, 15 or more) different transition metal atoms. Thus the samples in the methods discussed above may be labelled with four or more (e.g. 5, 6, 7, 8, 9, 10, 12, 13, 14, 15 or more) different transition metal atoms. These atoms associate with specific cellular targets, thereby permitting downstream detection by LA-ICP-MS. Data from the LA-ICP-MS can then be used to create an image of the sample.

The invention also provides a method of imaging a biological sample, wherein multiple cells of the sample are subjected to mass cytometry at a subcellular resolution.

The effectiveness of these techniques is demonstrated in reference 7, as also discussed below. This document describes mass cytometry using rare earth metals on antibodies to label target proteins in a biological sample. The sample is then analysed by an LA-ICP-MS system such as that described herein, and the simultaneous imaging of 32 proteins was demonstrated.

LA-ICP-MS and Mass Cytometry

The invention uses laser ablation coupled to inductively coupled plasma mass spectrometry (LA-ICP-MS) in a method of imaging a biological sample, such as a tissue sample. Different target molecules in the sample are labelled with different labelling atoms and LA-ICP-MS is then used across multiple cells of the labelled sample. By linking detected signals to the known positions of the laser ablations which gave rise to those signals the method permits localisation of the labelled target molecule to specific locations on the sample, and thus construction of an image of the sample.

LA-ICP-MS involves subjecting the sample to laser pulses which generate plumes of ablated material from the sample, and these plumes are transferred as aerosols to an ICP-MS instrument for analysis. The labelling atoms in the sample can be distinguished by MS and so their detection reveals the presence or absence of multiple targets in a plume.

The spatial resolution of signals generated in this way depends on two main factors: (i) the spot size of the laser, as signal is integrated over the total area which is ablated; and (ii) the speed at which a plume can be analysed, relative to the speed at which plumes are being generated, to avoid overlap of signal from consecutive plumes as mentioned above.

Thus, in order to analyse individual cells the invention uses a laser spot size which is no larger than these cells, and more specifically uses a laser spot size which can ablate material with a subcellular resolution. This size will depend on the particular cells in a sample, but in general the laser spot will have a diameter of less than 4 μm e.g. within the range 0.2-4 μm, 0.25-3 μm, or 0.4-2 μm. Thus a laser spot can have a diameter of about 3 μm, 2 μm, 1 μm, or 0.5 μm. In a preferred embodiment the laser spot diameter is within the range of 0.5-1.5 μm, or about 1 μm. Small spot sizes can be achieved using demagnification of wider laser beams and near-field optics. A laser spot diameter of 1 μm corresponds to a laser focus point of 1 μm, but the laser focus point can vary by +20% due to numerical aperture of the objective that transfers the laser beam onto the sample surface.

For rapid analysis of a sample a high frequency of ablation is needed, for example 10 Hz or more (i.e. 10 ablations per second, giving 10 plumes per second). In a preferred embodiment the frequency of ablation is within the range 10-200 Hz, within the range 15-100 Hz, or within the range 20-50 Hz. An ablation frequency of at least 20 Hz allows imaging of typical tissue samples to be achieved in a reasonable time. As noted above, at these frequencies the instrumentation must be able to analyse the ablated material rapidly enough to avoid substantial signal overlap between consecutive ablations. It is preferred that the overlap between signals originating from consecutive plumes is <10% in intensity, more preferably <5%, and ideally <1%. The time required for analysis of a plume will depend on the washout time of the ablation cell, the transit time of the plume aerosol to and through the ICP, and the time taken to analyse the ionised material.

Thus an ablation cell with a short washout time (e.g. 100 ms or less) is advantageous for use with the invention. One example of such an ablation cell is the ablation cell discussed hereinabove. A cell with a long washout time will either limit the speed at which an image can be generated or will lead to overlap between signals originating from consecutive sample spots (e.g. reference 8, which had signal duration of over 10 seconds). Therefore aerosol washout time is a key limiting factor for achieving high resolution without increasing total scan time. Ablation cells with washout times of <100 ms are known in the art. For example, reference 9 discloses an ablation cell with a washout time below 100 ms. A particularly suitable ablation cell was disclosed in reference 10 (see also reference 11) which has a washout time of 30 ms or less, thereby permitting a high ablation frequency (e.g. between 20-40 Hz) and thus rapid analysis. The examples herein demonstrate that the signals of plumes generated by 20 Hz laser ablation shots can be fully separated by this ablation cell, thereby enabling imaging of a large area in short time. Using methods of the invention, it is therefore possible to achieve a time per spatially resolved pixel in a final image of less than 100 ms.

The transit time of a plume aerosol to and through the ICP is easily controlled simply by positioning the ablation cell near to the ICP and by ensuring a sufficient gas flow to transport the aerosol at an appropriate speed directly to the ICP. Transport using argon and helium as described in reference 10 provides good results.

The time taken to analyse the ionised material will depend on the type of mass analyser which is used for detection of ions. For example, instruments which use Faraday cups are generally too slow for analysing rapid signals. Overall, the desired imaging speed (and thus ablation frequency), resolution (and thus laser spot size and ablation cell) and degree of multiplexing will dictate the type(s) of mass analyser which should be used (or, conversely, the choice of mass analyser will determine the speed, resolution and multiplexing which can be achieved).

Mass spectrometry instruments that detect ions at only one mass-to-charge ratio (m/Q, commonly referred to as m/z in MS) at a time, for example using a point ion detector, will give poor results in single cell imaging using multiple labels. Firstly, the time taken to switch between mass-to-charge ratios limits the speed at which multiple signals can be determined, and secondly, if ions are at low abundance then signals can be missed when the instrument is focused on other mass-to-charge ratios. Thus, although the instrument used in references 4 and 5 (Agilent 4500) is sensitive, its quadrupole-based detector is not well suited to imaging with multiple labels because, by design, ions of different mass-to-charge ratios pass through sequentially and so data acquisition for multiple labels is slow. Similarly, the instruments used in references 6 and 10 (Thermo Fisher ElementXR and Element2) analyse only one m/Q at a time and have a large settling time for magnet jumps when measuring multiple m/Q values over a range exceeding the range of an electrostatic field jump.

Thus it is preferred to use a technique which offers substantially simultaneous detection of ions having different m/Q values. For instance, instead of using a point ion detector, it is possible to use an array detector (e.g. see Chapter 29 of ref 12). Multi-collector sector field ICP-MS instruments can be used (e.g. the Thermo Scientific Neptune Plus, Nu Plasma II, and Nu Plasma 1700 systems), and in particular those having a Mattauch-Herzog geometry (e.g. the SPECTRO MS, which can simultaneously record all elements from lithium to uranium in a single measurement using a semiconductor direct charge detector). These instruments can measure multiple m/Q signals substantially simultaneously. Their sensitivity can be increased by including electron multipliers in the detectors. Array sector instruments are not ideal, however, because, although they are useful for detecting increasing signals, they are less useful when signal levels are decreasing, and so they are not well suited in situations where labels are present at highly variable concentrations.

The most preferred MS method for use with the invention is based on time-of-flight (TOF) detection, which can quasi-simultaneously register multiple masses in a single sample. In theory TOF techniques are not ideally suited to ICP ion sources because of their space charge characteristics, but it has been shown that TOF instruments can analyse an ICP ion aerosol rapidly enough and sensitively enough to permit feasible single-cell imaging (e.g. reference 7). Whereas TOF mass analyzers are normally unpopular for atomic analysis because of the compromises required to deal with the effects of space charge in the TOF accelerator and flight tube, imaging methods of the invention can be effective by detecting only the labelling atoms, and so other atoms (e.g. those having an atomic mass below 100) can be removed. This results in a less dense ion beam, enriched in the masses in (for example) the 100-250 dalton region, which can be manipulated and focused more efficiently, thereby facilitating TOF detection and taking advantage of the high spectral scan rate of TOF. Thus rapid imaging can be achieved by combining TOF detection with choosing labelling atoms that are uncommon in the sample and ideally having masses above the masses seen in an unlabelled sample e.g. by using the higher mass transition elements. Using a narrower window of label masses thus means that TOF detection to be used for efficient imaging.

Suitable TOF instruments are available from Tofwerk, GBC Scientific Equipment (e.g. the Optimass 9500 ICP-TOFMS), and Fluidigm Canada (e.g. the CyTOF™ and CyTOF™ 2 instruments). These CyTOF™ instruments have greater sensitivity than the Tofwerk and GBC instruments and are known for use in mass cytometry because they can rapidly and sensitively detect ions in the mass range of rare earth metals (particularly in the m/Q range of 100-200) [13]. Thus these are preferred instruments for use with the invention, and they can be used for imaging with the instrument settings already known in the art e.g. references 14 & 15. Their mass analysers can detect a large number of markers quasi-simultaneously at a high mass-spectrum acquisition frequency on the timescale of high-frequency laser ablation [6]. They can measure the abundance of labelling atoms with a detection limit of about 100 per cell, permitting sensitive construction of an image of the sample. Because of these features, mass cytometry can now be used to meet the sensitivity and multiplexing needs for imaging at subcellular resolution. Previously, mass cytometry has been used only to analyze cells in suspension, and information on cell-cell interactions within or tumor microenvironments has therefore been lost. By combining the mass cytometry instrument with a high-resolution laser ablation system and a rapid-transit low-dispersion ablation chamber it has been possible to permit construction of an image of the sample with high multiplexing on a practical timescale. Further details on mass cytometry can be found in references 3 and 16.

The choice of wavelength and power of the laser used for ablation of the sample can follow normal usage in cellular analysis by ICP-MS. The laser must have sufficient fluence to cause ablation to a desired depth, without substantially ablating the supporting sample holder. A laser fluence of between 2-5 J/cm$^2$ at 20 Hz is typically suitable e.g. from 3-4 J/cm$^2$ or about 3.5 J/cm$^2$. Ideally a single laser pulse will be sufficient to ablate cellular material for analysis, such that the laser pulse frequency matches the frequency with which ablation plumes are generated. Lasers will usually be excimer or exciplex lasers. Suitable results can be obtained using an argon fluoride laser ($\lambda$=193 nm). Using an aperture of 25 µm this laser can be imaged by 25-fold demagnification onto the samples to give a spot size with a 1 µm diameter. Pulse durations of 10-15 ns with these lasers can achieve adequate ablation. Femtosecond lasers (i.e. with pulse durations <1 ps) can also be used, and would be beneficial due to reduced heat transfer into the sample, but they are very expensive and good imaging results can be achieved without them.

Overall, the laser pulse frequency and strength are selected in combination with the response characteristics of the MS detector to permit distinction of individual laser ablation plumes. In combination with using a small laser spot and an ablation cell having a short washout time, rapid and high resolution imaging is now feasible.

Thus the invention provides an LA-ICP-MS system in which the washout time of the ablation cell is less than 100 ms. In some embodiments, the washout time may be less than 90 ms, less than 80 ms, less than 70 ms, less than 60 ms, less than 50 ms, less than 40 ms or less than 30 ms. In some embodiments, the mass analyser in the LA-ICP-MS system is a TOF mass analyser. In some embodiments, the LA-ICP-MS system comprises a biological sample.

The invention also provides an LA-ICP-MS system comprising:

(i) a biological sample wherein at least three different target molecules in the biological sample have been labelled with at least three different labelling atoms, and (ii) a laser which has been adapted to ablate the biological sample with a spot size of less than 4 µm.

Constructing an Image

LA-ICP-MS can provide signals for multiple labelling atoms in plumes. Detection of a label in a plume reveals the presence of its cognate target at the position of oblation. By generating a series of plumes at known spatial locations on the sample's surface the MS signals reveal the location of the labels on the sample, and so the signals can be used to construct an image of the sample. By labelling multiple targets with distinguishable labels it is possible to associate the location of labelling atoms with the location of cognate targets, so the invention can build complex images, reaching levels of multiplexing which far exceed those achievable using existing techniques. Images generated by the methods of the invention can reproduce the staining patterns and the proportion of cells expressing a given marker as determined by IFM, thereby confirming the invention's suitability for imaging (see e.g. reference 7).

Ideally the image will be constructed by performing raster scanning of the laser over the sample. The spacing of consecutive ablations in the raster scan (step size), and between adjacent lines in the raster scan, is ideally the same as the laser spot size which is used (e.g. 1 µm spacing for a 1 µm laser spot) in order to achieve complete coverage of a region of interest. In some embodiments, however, methods can use a step size which is smaller than the laser spot size (e.g. at least 2×, 4×, or 5× smaller) as this can lead to smaller ablation areas and thus improve imaging resolution. For achieving the scanning it is possible to move the laser, but it is usually more convenient to move the ablation cell (or the contents of the cell). The movement speed will depend on the ablation frequency and the raster spacing e.g. with 1 µm raster spacing and 20 Hz ablation the ablation cell will have a translation speed of 20 µm/s. Support stages which can achieve step sizes of 1 µm of less are available e.g. with 500 nm or 200 nm step sizes (or even less).

Methods of the invention are generally used to create two-dimensional (2D) images of a sample, based on the contents of an ablated surface layer. 3D images of a tissue can be prepared by assembling stacks of 2D images (in a x,y plane) from sections of a single sample which are adjacent in the z-axis. As an alternative to assembling 2D images in this way, however, methods of the invention can also be used for direct 3D imaging. This can be achieved in various ways. For instance, if the ablation causes vaporisation with a substantially constant depth then repeated ablation at a single x,y point reveals progressively deeper information in the z-axis. If ablation does not have a substantially constant depth then the volume of ablated material can be measured (e.g. relative to a standard of known volume), and this volume can be easily converted to a z-axis depth. Where 3D imaging is performed it is possible to perform multiple z-axis ablations while x,y location is maintained ('drilling'), or to ablate a sample layer by layer (i.e. perform ablations of a x,y area before moving to a deeper z-axis layer). Layer-by-layer ablation is preferred. Accuracy of 3D imaging is limited by factors such as re-deposition of ablated material, the ability to maintain a constant ablation depth, and the ability of labels to penetrate into the sample, but useful results can still be achieved within the boundaries of these limitations.

Assembly of signals into an image will use a computer and can be achieved using known techniques and software packages. For instance, reference 5 used the GRAPHIS package from Kylebank Software, but other packages such as TERAPLOT can also be used. Imaging using MS data from techniques such as MALDI-MSI is known in the art e.g. reference 17 discloses the 'MSiReader' interface to view and analyze MS imaging files on a Matlab platform, and reference 18 discloses two software instruments for rapid data exploration and visualization of both 2D and 3D MSI data sets in full spatial and spectral resolution e.g. the 'Datacube Explorer' program.

Images obtained using methods of the invention can be further analysed e.g. in the same way that IHC results are analysed. For instance, the images can be used for delineating cell sub-populations within a sample, and can provide information useful for clinical diagnosis. Similarly, SPADE analysis can be used to extract a cellular hierarchy from the high-dimensional cytometry data which methods of the invention provide [19].

Labelling of the Biological Sample

The invention provides images of samples which have been labelled with a plurality of different labelling atoms, wherein the labelling atoms are detected in laser-ablated plumes by ICP-MS. The reference to a plurality of different atoms means that more than one atomic species is used to label the sample. These atomic species can be distinguished using ICP-MS (e.g. they have different m/Q ratios), such that the presence of two different labelling atoms within a plume gives rise to two different MS signals.

The invention is suitable for the simultaneous detection of many more than two different labelling atoms, permitting multiplex label detection e.g. at least 3, 4, 5, 10, 20, 30, 32, 40, 50 or even 100 different labelling atoms. Labelling atoms can also be used in a combinatorial manner to even further increase the number of distinguishable labels. The examples demonstrate the use of 32 different labelling atoms in an imaging method, but LA-ICP-MS is intrinsically suitable for parallel detection of higher numbers of different atoms e.g. even over 100 different atomic species [13]. By labelling different targets with different labelling atoms it is possible to determine the cellular location of multiple targets in a single image.

Labelling atoms that can be used with the invention include any species that are detectable by LA-ICP-MS and that are substantially absent from the unlabelled sample. Thus, for instance, $^{12}C$ atoms would be unsuitable as labelling atoms because they are naturally abundant, whereas $^{11}C$ could in theory be used because it is an artificial isotope which does not occur naturally. In preferred embodiments, however, the labelling atoms are transition metals, such as the rare earth metals (the 15 lanthanides, plus scandium and yttrium). These 17 elements provide many different isotopes which can be easily distinguished by ICP-MS. A wide variety of these elements are available in the form of enriched isotopes e.g. samarium has 6 stable isotopes, and neodymium has 7 stable isotopes, all of which are available in enriched form. The 15 lanthanide elements provide at least 37 isotopes that have non-redundantly unique masses. Examples of elements that are suitable for use as labelling atoms include Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Scandium (Sc), and Yttrium (Y). For example, the invention can use any of the isotopes of the lanthanides as listed in Tables 1 to 5. In addition to rare earth metals, other metal atoms are suitable for detection by ICP-MS e.g. gold (Au), platinum (Pt), iridium (Ir), rhodium (Rh), bismuth (Bi), etc. The use of radioactive isotopes is not preferred as they are less convenient to handle and are unstable e.g. Pm is not a preferred labelling atom among the lanthanides.

In order to facilitate TOF analysis (see above) it is helpful to use labelling atoms with an atomic mass within the range 80-250 e.g. within the range 80-210, or within the range 100-200. This range includes all of the lanthanides, but excludes Sc and Y. The range of 100-200 permits a theoretical 101-plex analysis by using different labelling atoms, while permitting the invention to take advantage of the high spectral scan rate of TOF MS. As mentioned above, by choosing labelling atoms whose masses lie in a window above those seen in an unlabelled sample (e.g. within the range of 100-200), TOF detection can be used to provide rapid imaging at biologically significant levels.

Labelling the biological sample generally requires that the labelling atoms are attached to one member of a specific binding pair (sbp). This labelled sbp is contacted with a sample such that it can interact with the other member of the sbp (the target sbp member) if it is present, thereby localising the labelling atom to a specific location in the sample. The sbp that delivers the label to the target molecule is also referred to herein as a specific labelling construct. The method of the invention then detects the presence of the labelling atom at this specific location and translates this information into an image in which the target sbp member is present at that location. Rare earth metals and other labelling atoms can be conjugated to sbp members by known techniques e.g. reference 20 describes the attachment of lanthanide atoms to oligonucleotide probes for ICP-MS detection, reference 21 describes the use of ruthenium to label oligonucleotides, and Fluidigm Canada sells the MaxPar™ metal labelling kits which can be used to conjugate over 30 different labelling atoms to proteins (including antibodies).

Various numbers of labelling atoms can be attached to a single sbp member, and greater sensitivity can be achieved when more labelling atoms are attached to any sbp member. For example greater than 10, 20, 30, 40, 50, 60, 70, 80, 90 or 100 labelling atoms can be attached to a sbp member. For example, monodisperse polymers containing multiple monomer units may be used, each containing a chelator such as DTPA. DTPA, for example, binds 3+ lanthanide ions with a dissociation constant of around $10^{-6}$ M [3]. These polymers can terminate in a thiol-reactive group (e.g. maleimide) which can be used for attaching to a sbp member. For example the thiol-reactive group may bind to the Fc region of an antibody. Other functional groups can also be used for conjugation of these polymers e.g. amine-reactive groups such as N-hydroxy succinimide esters, or groups reactive against carboxyls or against an antibody's glycosylation. Any number of polymers may bind to each sbp member. Specific examples of polymers that may be used include straight-chain ("X8") polymers or third-generation dendritic ("DN3") polymers, both available as MaxPar™ reagents. Use of metal nanoparticles can also be used to increase the number of atoms in a label.

As mentioned above, labelling atoms are attached to a sbp member, and this labelled sbp member is contacted with the sample where it can find the target sbp member (if present), thereby forming a labelled sbp. The labelled sbp member can comprise any chemical structure that is suitable for attaching to a labelling atom and then for imaging according to the invention.

In general terms, methods of the invention can be based on any sbp which is already known for use in determining the location of target molecules in samples (e.g. as used in IHC or fluorescence in situ hybridisation, FISH), but the sbp member which is contacted with the sample will carry a labelling atom which is detectable by ICP-MS. Thus the invention can readily be implemented by using available IHC and FISH reagents, merely by modifying the labels which have previously been used e.g. to modify a FISH probe to carry a label which can be detected by ICP-MS.

The sbp may comprise any of the following: a nucleic acid duplex; an antibody/antigen complex; a receptor/ligand pair; or an aptamer/target pair. Thus a labelling atom can be attached to a nucleic acid probe which is then contacted with a sample so that the probe can hybridise to complementary nucleic acid(s) therein e.g. to form a DNA/DNA duplex, a DNA/RNA duplex, or a RNA/RNA duplex. Similarly, a labelling atom can be attached to an antibody which is then contacted with a sample so that it can bind to its antigen. A labelling atom can be attached to a ligand which is then contacted with a sample so that it can bind to its receptor. A labelling atom can be attached to an aptamer ligand which is then contacted with a sample so that it can bind to its target. Thus labelled sbp members can be used to detect a variety of targets in a sample, including DNA sequences, RNA sequences, proteins, sugars, lipids, or metabolites.

In a typical embodiment of the invention the labelled sbp member is an antibody. Labelling of the antibody can be achieved through conjugation of one or more labelling atom binding molecules to the antibody, for example using the MaxPar™ conjugation kit as described above. Antibodies which recognise cellular proteins that are useful for imaging are already widely available for IHC usage, and by using labelling atoms instead of current labelling techniques (e.g. fluorescence) these known antibodies can be readily adapted for use in methods of the invention, but with the benefit of increasing multiplexing capability. Antibodies used with the invention can recognise targets on the cell surface or targets within a cell. Antibodies can recognise a variety of targets e.g. they can specifically recognise individual proteins, or can recognise multiple related proteins which share common epitopes, or can recognise specific post-translational modifications on proteins (e.g. to distinguish between tyrosine and phospho-tyrosine on a protein of interest, to distinguish between lysine and acetyl-lysine, to detect ubiquitination, etc.). After binding to its target, labelling atom(s) conjugated to an antibody can be detected to reveal the location of that target in a sample.

The labelled sbp member will usually interact directly with a target sbp member in the sample. In some embodiments, however, it is possible for the labelled sbp member to interact with a target sbp member indirectly e.g. a primary antibody may bind to the target sbp member, and a labelled secondary antibody can then bind to the primary antibody, in the manner of a sandwich assay. Usually, however, the invention relies on direct interactions, as this can be achieved more easily and permits higher multiplexing. In both cases, however, a sample is contacted with a sbp member which can bind to a target sbp member in the sample, and at a later stage label attached to the target sbp member is detected.

One feature of the invention is its ability to detect multiple (e.g. 10 or more, and even up to 100 or more) different target sbp members in a sample e.g. to detect multiple different proteins and/or multiple different nucleic acid sequences. To permit differential detection of these target sbp members their respective sbp members should carry different labelling atoms such that their signals can be distinguished by ICP-MS. For instance, where ten different proteins are being detected, ten different antibodies (each specific for a different target protein) can be used, each of which carries a unique label, such that signals from the different antibodies can be distinguished. In some embodiments, it is desirable to use multiple different antibodies against a single target e.g. which recognise different epitopes on the same protein. Thus a method may use more antibodies than targets due to redundancy of this type. In general, however, the invention will use a plurality of different labelling atoms to detect a plurality of different targets.

If more than one labelled antibody is used with the invention, it is preferable that the antibodies should have similar affinities for their respective antigens, as this helps to ensure that the relationship between the quantity of labelling atoms detected by LA-ICP-MS and the abundance of the target antigen in the sample will be more consistent across different sbp's (particularly at high scanning frequencies).

If a target sbp member is located intracellularly, it will typically be necessary to permeabilize cell membranes before or during contacting of the sample with the labels. For example when the target is a DNA sequence but the labelled sbp member cannot penetrate the membranes of live cells, the cells of the sample can be fixed and permeabilised. The labelled sbp member can then enter the cell and form a sbp with the target sbp member. In this respect, known protocols for use with IHC and FISH can be utilised.

Usually, a method of the invention will detect at least one intracellular target and at least one cell surface target. In some embodiments, however, the invention can be used to detect a plurality of cell surface targets while ignoring intracellular targets. Overall, the choice of targets will be determined by the information which is desired from the method, as the invention will provide an image of the locations of the chosen targets in the sample.

Typically, where at least one of a plurality of different target molecules in the tissue sample is labelled with at least one different labelling atom, each different target is labelled with a different labelling atom, so that the presence of absence of each target can be determined on the basis of the presence of absence of a specific labelling atom. In some instances, it however, multiple targets may be labelled with the same atom. In the instance of a protein, this may be because the multiple targets labelled with the same atom share a common epitope, meaning that the different proteins are bound by the same antibody. One example of such a situation would be the labelling of all IgG molecules with an antibody which binds to the Fc region of the antibody, even though the IgG molecules may have variable domains of difference sequence and bind to a range of antigens. Alternatively, a protein bound by an antibody may be a subunit of a range of different multimer complexes, meaning that each complex containing the subunit will be labelled by the same antibody. An example of this is found in antibodies which bind to certain multimeric cytokines or receptors, for example the p40 subunit is part of both the IL-12 cytokine and the IL-23 cytokine. In the case of a nucleic acid, the same principle could apply where various nucleic acid sequences share a common motif. One example of this situation is a nucleic acid which binds to Alu repeats.

Biological Samples

The invention provides methods and laser ablation cells, ion sources, ablation apparatus and systems for imaging a biological sample. In some instances, this sample is a tissue sample. The tissue sample comprises a plurality of interacting cells, and the method subjects a plurality of these cells to laser ablation in order to provide an image of these cells in the tissue sample. In general, the invention can be used to analyse tissue samples which are now studied by IHC techniques, but with the use of labels which are suitable for detection by LA-ICP-MS.

Any suitable tissue sample can be used in the methods described herein. For example, the tissue can be epithelium tissue, muscle tissue, nerve tissue, etc., and combinations thereof. For diagnostic or prognostic purposes the tissue can be from a tumor. In some embodiments a sample may be from a known tissue, but it might be unknown whether the sample contains tumor cells. Imaging can reveal the presence of targets which indicate the presence of a tumor, thus facilitating diagnosis. The tissue sample may comprise breast cancer tissue, for example human breast cancer tissue or human mammary epithelial cells (HMLE). The tissue sample may comprise formalin-fixed, paraffin-embedded (FFPE) tissue. The tissues can be obtained from any living multicellular organism, but will usually be human.

The tissue sample will usually be a section e.g. having a thickness within the range of 2-10 µm, such as between 4-6 µm. Techniques for preparing such sections are well known from the field of IHC e.g. using microtomes, including dehydration steps, including embedding, etc. Thus a tissue may be chemically fixed and then sections can be prepared in the desired plane. Cryosectioning or laser capture microdissection can also be used for preparing tissue samples. Samples may be permeabilised e.g. to permit of reagents for labelling of intracellular targets (see above).

The size of a tissue sample to be analysed will be similar to current IHC methods, although the maximum size will be dictated by the laser ablation apparatus, and in particular by the size of sample which can fit into its ablation cell. A size of up to 5 mm×5 mm is typical, but smaller samples (e.g. 1 mm×1 mm) are also useful (these dimensions refer to the size of the section, not its thickness).

In addition to being useful for imaging tissue samples, the invention can instead be used for imaging of cellular samples such as monolayers of adherent cells or of cells which are immobilised on a solid surface (as in conventional immunocytochemistry). These embodiments are particularly useful for the analysis of adherent cells that cannot be easily solubilized for cell-suspension mass cytometry. Thus, as well as being useful for enhancing current immunohistochemical analysis, the invention can be used to enhance immunocytochemistry. The invention can also be used for imaging biofilms. The analysis of biofilms is important in a medical setting because biofilms of infective reagents can form on mucous membranes in the body, or, for example, on indwelling catheters.

After being prepared, the sample will be placed into a laser ablation cell and then subjected to analysis according to the invention.

Combinations With Other Techniques

The method disclosed herein can also be used in techniques for diagnosing and treating diseases, by characterising samples from patients. In essence, the method can be used for any purpose for which IHC is used currently (as known in the art, and summarised briefly, for example, in reference 22). Thus the invention provides a method of diagnosing a disease in a patient comprising:

(i) determining the quantity, presence and/or location of at least one of a plurality of target molecules in a biological sample from said patient, wherein each of the at least one target molecules has been labelled with an atom which can be distinguished by LA-ICP-MS to identify each of the at least one different target molecules, by performing LC-ICP-MS on the tissue sample to produce an image of the sample on which the quantity, presence and/or location of the at least one of a plurality of target molecules is provided; and (ii) comparing the image obtained in step (i) to images obtained from a subject known to be suffering from a disease, thereby diagnosing the disease in the patient.

It is then possible to administer a treatment to the patient that is used to treat the disease identified in step (ii).

The invention also provides a method of monitoring the effectiveness of a treatment in a patient comprising:

(i) determining the quantity, presence and/or location of at least one of a plurality of target molecules in a biological sample from said patient, wherein each of the at least one target molecules has been labelled with an atom which can be distinguished by LA-ICP-MS to identify each of the at least one different target molecules, by performing LC-ICP-MS on the tissue sample to produce an image of the sample on which the quantity, presence and/or location of the at least one of a plurality of target molecules is provided;

(ii) comparing the image obtained in step (i) to images of the tissue previously obtained from the patient, thereby determining whether the quantity, presence and/or location of the least one of a plurality of target molecules has been modulated by the treatment, and correlating this modulation with the effectiveness or ineffectiveness of the treatment.

Based on this, it is then possible to decide whether to continue or to alter the treatment based on whether the treatment is effective against the disease.

The specific procedure used in step (i) of these methods can be any of the specific LC-ICP-MS methods discussed herein. By comparing the image is meant that the LC-ICP-MS image from the subject known to be suffering from a disease (i.e. what would commonly be called a reference standard) is analysed for the quantity, presence and/or location of at least one of a plurality of target molecules and then the image generated in step (i) of the method is analysed in the same way. If the quantity, presence and/or location of the marker(s) under analysis is seen to be similar between the patient and the reference standard from the subject, it is indicative that the patient may be suffering from the same disease as the patient (e.g. cancer). This diagnosis thereby permits an appropriate treatment strategy to be decided upon for the patient.

Diagnostic, monitoring and treatment aspects of the invention relate to the following conditions and processes:

cancers such as leukemia, acute leukemia, acute lymphoblastic leukemia (ALL), acute lymphocytic leukemia, B-cell, T-cell or F AB ALL, acute myeloid leukemia (AML), acute myelogenous leukemia, chromic myelocytic leukemia (CML), chronic lymphocytic leukemia (CLL), hairy cell leukemia, myelodyplastic syndrome (MDS), a lymphoma, Hodgkin's disease, a malignamt lymphoma, nonhodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometiral cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like, in particular, breast and prostate cancer; diagnosis of tumors of uncertain histogensesis (e.g. metastatic tumors from an unknown primary tumour);

diseases characterised by the build-up of amyloid plaques, such as Alzheimer's disease or Parkinson's disease;

confirmation of infectious agents in a biological sample;

precise diagnosis of different forms of muscle dystrophy and the like.

EXAMPLES i. Experimental

Manufacture of Laser Ablation Cell

A cell top 10 was manufactured from a rectangular cuboid of acrylic glass (poly (methyl methacrylate), PMMA). A longitudinal hole of 3 mm inner diameter was drilled through the cuboid along the long axis, forming the flow channel 11. In the top wall portion 17 of the cell top 10, a transversal, slightly elliptically shaped hole with length L=4.5 mm and a width of 1.5 mm was formed and was closed by an UV transparent silica window 16. A lateral opening 14 of similar dimensions as the hole on the top side was formed in the bottom wall portion 15 of the cell top 10. The bottom wall portion 15 was then machined to reduce the minimum thickness w of the bottom wall portion in the region of the flow channel 11 to approximately 50 micrometers. The total length of the flow channel 11 was about 50 mm.

A cell bottom 10 was manufactured from another PMMA cuboid. A cylindrical sample chamber 21 having a diameter of approximately 23 mm was milled into the cuboid. A radially extending hole was drilled into the cell bottom to form a sheath gas inlet 22. The sheath gas inlet extended at an angle of 10° relative to the flow channel 11. A sample 23 was placed in the sample chamber 21. The cell bottom 20 was mounted to the cell top 10 with the aid of four screws (not shown in the drawings). No spacer or seal was required, but a spacer or seal may optionally be provided to better seal of the contact region between the cell top 10 and the cell bottom 20. The top surface 24 of the sample 23 faced the lateral opening 14. The distance d between the top surface 24 of the sample 23 and the bottom wall portion 15 was about 350 micrometers. Thus, the total distance between the sample surface 24 and the center axis of the flow channel 11 was approximately 1.9 millimeters (radius of the flow channel=1.50 mm, wall thickness w=0.05 mm, distance d=0.35 mm).

Experimental Set-Up for Tube Cell Performance, Optimization and Characterization An ArF excimer laser system (Lambda Physik, Gottingen, Germany) with homogenized laser beam profile was coupled to an Agilent 7500cs ICP-Quadrupole-MS instrument (ICP-Q-MS, Agilent Technologies, Waldbronn, Germany). Laser fluence was 17.3 J/cm$^2$. In order to improve the confidence level, all data points were derived from 3×3 single shot matrix scans (unless otherwise stated) with laser spot size of 10 µm and spacing of 15 µm between adjacent shots. The transfer tube to the ICP torch consisted of a 3 mm inner diameter PTFE (polytetrafluoroethylene) tubing connected to the mixed-gas outlet 13. A similar tube was used as a feed tube to the Ar inlet 12. The Ar carrier gas flow was adjusted to 1.1 L/min. The 50 cm long transfer tube was directly connected to the ICP torch without changing the diameter. The He sheath gas flow provided through the sample chamber was adjusted to 0.6 L/min. Tube cell performance measurements were carried out using a dwell time of 10 ms. In order to describe the washout of the cell, single isotope $^{27}$Al acquisitions during 1 Hz, 10 Hz and 30 Hz laser ablations on NIST 610 reference glass were performed. The ICP was operated at 1470 W and the quadrupole MS was set to 1 point per peak in peak hopping mode.

Optimization of various operational parameters was carried out, including: the gap distance between carrier tube opening and the sample surface; the Ar carrier gas flow rate; and the He sheath gas flow rate. When optimizing one parameter, the other two were set to the 'pre-optimized' conditions, based on the preliminary optimization, e.g. gap distance at 350 µm, Ar flow at 1.1 L/min, He flow at 0.6 L/min. The data were evaluated based on the normalized peak width, which is the peak width divided by the total counts collected within each peak (peak area). For each peak, full width at 1% maximum (FW0.01M) was used to determine the peak width. In case the 1% maximum position did not coincide with any data point, a linear interpolation of the nearest two points was applied. For the peak area, all data points within the peak width were integrated and no interpolation was required, since peak tailings contributed to less than 1% of the total counts.

The characterization of the cell for routine analysis was carried out using the same parameters as described above. However, multiple isotopes from low, mid to high m/Q were recorded in different runs. Peak area sensitivities were abundance corrected.

Sample Preparation for Imaging of "Hard" Matter

A sample for demonstrating imaging capabilities was produced by a laser-induced forward transfer method. For the preparation of the donor substrate, a high quality fused silica glass was covered with a UV-absorbing triazene polymer (TP) layer, as a sacrificial dynamic release layer (DRL), on which different thin film materials were deposited. In the transfer procedure, a 308 nm XeCl excimer laser beam was imaged on an 'ETH' (or 'PSI') hollow mask and 4 fold demagnified before impacting the back side of the donor substrate. TP-DRL was ablated and the generated shockwave propelling the thin film toward a glass receiver substrate coated with PEDOT:PSS (poly(3,4-ethylenedioxythiophene) blended with poly(styrenesulfonate)). The sample was prepared by a 60 nm thick Au 'ETH' thin layer on bottom and an 80 nm Ag 'PSI' on top (Au/Ag). To control the deposition of the two logos by scanning electron microscope (SEM), a 5 nm Pt thin film was uniformly coated on the receiver substrate after the pattern deposition.

Tissue Sample Preparation

A formalin-fixed paraffin-embedded human epidermal growth factor receptor 2 (HER2)-enriched breast cancer tissue was sectioned at 6 μm. The sample was processed on the Discovery XT platform (Ventana Medical Systems) under CC1m epitope recovery conditions. Afterwards, the sample was blocked for 30 minutes with phosphate buffered saline (PBS)/1% bovine serum albumin (BSA)/0.1% Triton X, and incubated with 200 μL $^{165}$Ho tagged anti-HER2 at 5 μg/mL for 50 minutes. The sample was washed three times in PBS/0.1% Triton X and dried at room temperature. For antibody conjugation with $^{165}$Ho, a commercial MAXPAR antibody labeling kit (DVS Sciences) was employed.

Instrumentation and Operating Conditions for Imaging of "Hard" Matter

A similar configuration as described for the tube cell characterization was used for the experiments. An area of 852×408 μm$^2$ was covered by 10 Hz repetition rate line scans. The distance between successive laser shots and the lateral distance between line scans were both 4 μm, based on a 4 μm laser crater. The actual laser beam size was 1-2 μm. However, a larger affected area was observed, which can be explained by an enlarged heat penetration volume (high thermal diffusion in the metallic thin films, and ns light-material interaction time). Three isotopes, $^{167}$Ag, $^{195}$Pt and $^{197}$Au, were measured in peak hopping mode with 600 μs dwell time for each isotope. However, due to an instrument quadrupole-settling time of a few milliseconds for each isotope, the reading of an entire set of isotopes could not be completed in less than 10 ms. Obviously, such a large overhead fraction (low duty cycle) does limit signal quality obtainable during fast, high resolution imaging experiments. Data analysis was based on the integration of each single shot signal (trapezium integration scheme).

Instrumentation and Operating Conditions for Tissue Imaging

Tissue imaging was conducted on an Element2 (Thermo Fisher Scientific) ICPMS coupled to an ArF excimer laser at ~1 μm spatial resolution. The operating conditions were optimized for maximum sensitivity of fast transient signals. Therefore, only $^{165}$Ho was recorded. For image analysis, the sample was scanned line by line at a laser frequency of 20 Hz and an image pixel size of 1×1 μm$^2$. Dwell time of the MS was set to 50 ms, in accordance with the laser ablation rate applied.

B. Results and Discussion

Tube Cell Optimization

Figure 6:
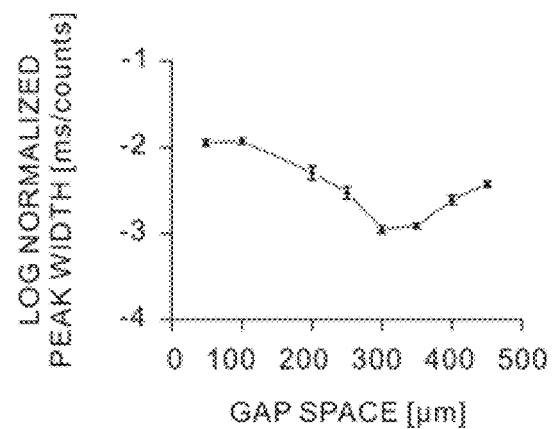
FIG. 6 shows diagrams illustrating the results of optimizations of the performance of the laser ablation cell by varying (a) the gap space between the sample surface and the lateral opening; (b) the carrier gas (Ar) flow rate; and (c) the sheath gas (He) flow rate; all diagrams show peak width normalized to peak area based on full width at 1% maximum criterion.
Figure 6:
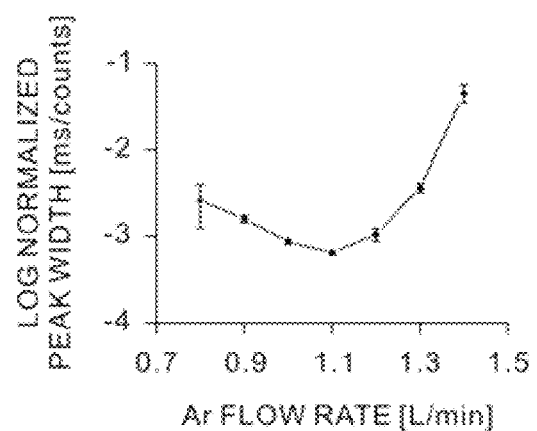
Figure 6:
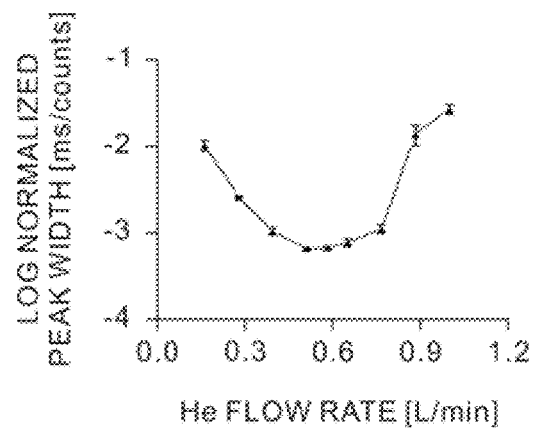

The dependence of the dispersion on the gap between the tube cell bottom and the sample surface is depicted in FIG. 6(a). The plotted peak widths were normalized to the total counts collected in FW0.01M. A minimum peak width at a gap width of ~350 μm was observed. Using this optimized gap distance, the Ar and He gas flow rate optimizations were carried out. The corresponding results are shown in FIGS. 6(b) and (c) based on the normalized peak widths. All three optimizations yield an evident minimum of ~$10^{-3}$ ms/counts for the normalized peak width. All measurements reported in the following sections were conducted using the optimized values for sample gap and gas flow rates. Depending on different setups, such optimization values may vary.

Experimental Evaluation of the Tube Cell

The tube cell was characterized using a laser frequency of ~1 Hz. Typical transient signals (shown in log-scale) are summarized in FIG. 7(a). A single washout signal of a major element lasted around 30 ms for FW0.01M. The transient peak has still a slightly asymmetric shape, tailing slightly which is caused by delayed washout of the aerosol. After the peak maxima, signals dropped down for more than 2 orders of magnitude within 20 ms, which represents more than 99.98% of the total integrated signal. The residual fraction of the total signal (0.02% integrated signal area) was found in the tail of the peak which reached background after 40-50 ms. The slope of the second signal decay is different than for the fast washout, indicating a different process, which is suspected to be related to the uptake of redeposited material from the surface. This is most likely due to the flow of the He sheath gas into the tube cell bottom opening, which is parallel to the laser plume injection, which flushes the area around the crater most efficiently. Spacing the single shots by 1 s blank indicates that no further sample removal occurs.

Figure 7:
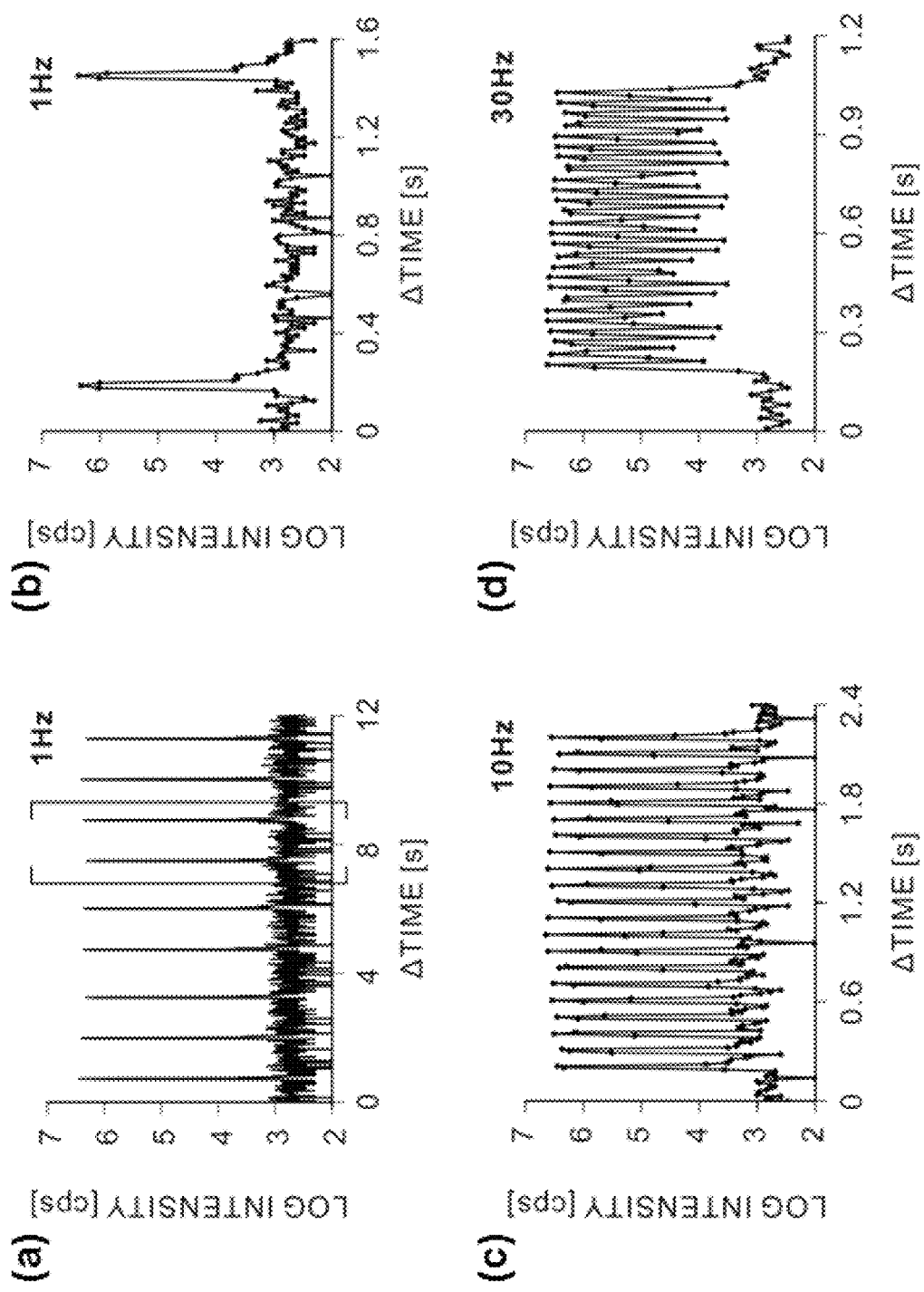
FIG. 7 shows diagrams illustrating the performance of the laser ablation cell as demonstrated by $^{27}$Al intensity in a mass spectrometer at various repetition rates: (a) transient signal for a repetition rate of approximately 1 Hz; (b) enlarged view of the bracketed portion of part (a); (c) transient signal for a repetition rate of approximately 10 Hz; (d) transient signal for a repetition rate of approximately 30 Hz.

FIG. 7(b) shows the transient signal acquired at a laser frequency of 10 Hz. The peak width and shape were similar to those signals measured at 1 Hz. Further increase in the laser frequency using a 30 Hz line scan is shown in FIG. 7(c). The width and shape of the peaks were similar to the signals measured at 1 Hz and 10 Hz. The signal structure indicates that two adjacent peaks cannot be separated to background from each other. However, the overlapping between two successive peaks is less than 1% in intensity. Therefore it can be concluded that even 30 Hz would allow to image concentration differences as large as two orders of magnitude, which makes this ablation cell very attractive for laser ablation imaging. The entire evaluation demonstrates that the washout is significantly improved into the 30-50 ms time range.

Tube Cell Characterization for Broad Isotope Range

Figure 8:
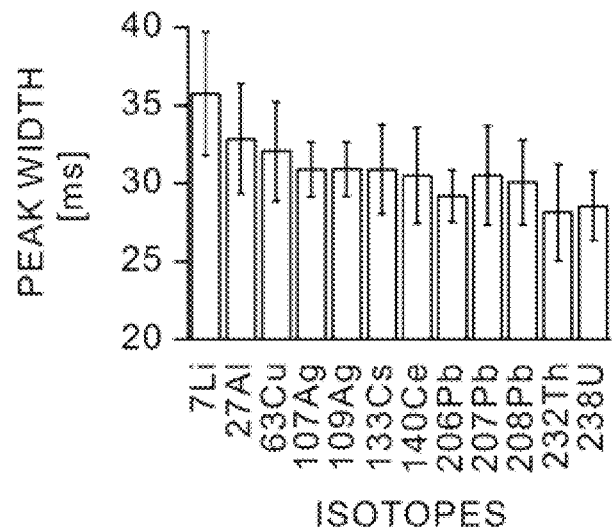
FIG. 8 shows diagrams illustrating the characterization of the laser ablation cell for various isotopes; (a) peak width; (b) abundance normalized sensitivity calculated from peak area.
Figure 8:
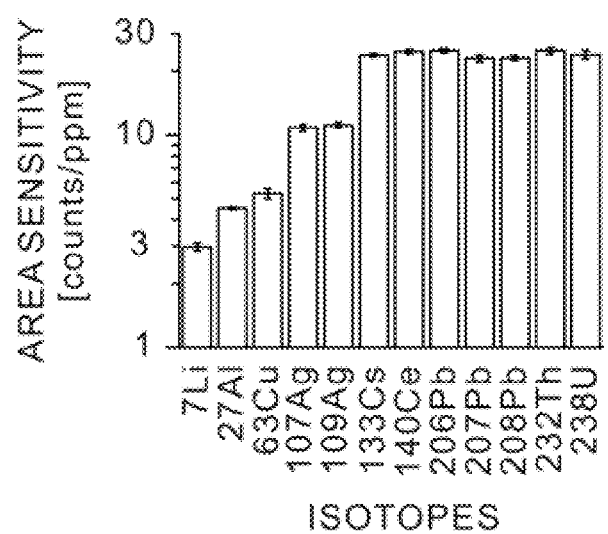

Further characterizations of the tube cell performance are documented in FIG. 8. Peak widths and sensitivities calculated from peak areas are shown for different isotopes from low m/Q ($^7$Li) up to high m/Q ($^{238}$U). As seen from FIG. 8(a), the mean peak widths of all the isotope measurements fall into a narrow range of 30-35 ms. The reported signal durations were calculated based on FW0.01M. The standard deviations across the m/Q range are most likely the result of the ablated mass, aliasing effects, and fluctuations due to differences in the gas flow dynamics. FIG. 8(b) shows furthermore the normalized sensitivities for the peak area, which were determined using 10 μm craters in single shot ablation mode. Compared to commonly used ablation cell setups in single shot mode, the peak area sensitivities improved by a factor of 10. This is not related to improved sample transport efficiency or improved ionization and purely based on the preserved sample density from the ablation site to the ICP.

Fast Imaging by Sequential Q-MS

Figure 9:
FIG. 9 shows images obtained for a Pt coated test pattern with an Au film in the form of letters "ETH" and an overlaid Ag film in the form of letters "PSI"; imaging was carried out by (a) optical microscopy; (b) scanning electron microscopy; (c) and (d) LA-ICP-Quadrupole-MS employing the laser ablation cell of FIG. 1.
Figure 9:
Figure 9:
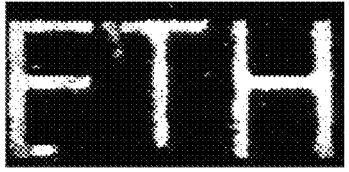
Figure 9:
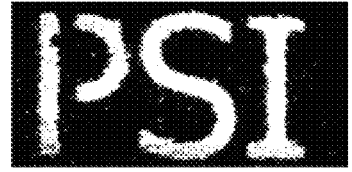
Figure 10:
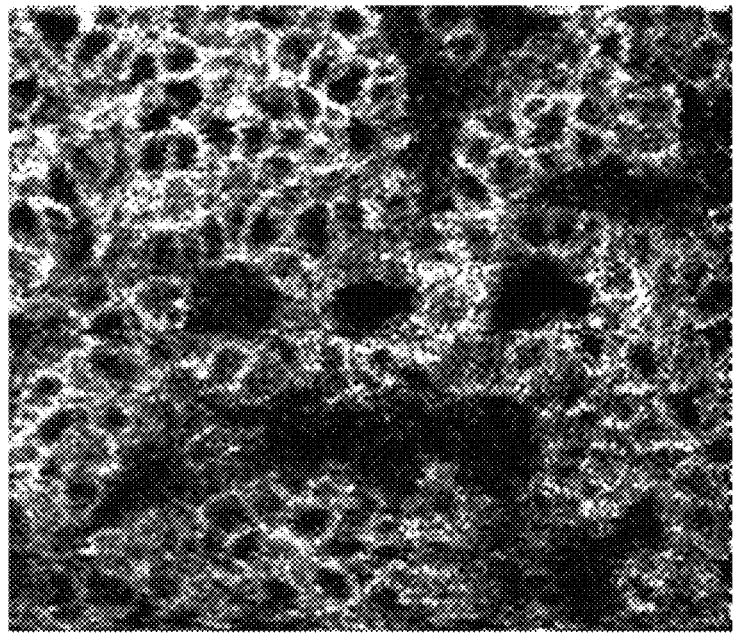
FIG. 10 illustrates an image of human epidermal growth factor receptor 2 (HER2) distribution in a thin section cut of a breast cancer tissue obtained by LA-ICP-Single-Detector-Sector-Field-MS.

The "hard" sample was studied by various imaging techniques. The results are illustrated in FIG. 9. The characteristic details of the pattern were imaged first by optical microscopy (FIG. 9(a)) and scanning electron microscopy (SEM, FIG. 9(b)). These images were used to evaluate the quality of the high sensitivity, high spatial resolution LA-ICPMS for $^{197}$Au (FIG. 9(c)) and $^{107}$Ag (FIG. 9(d)). The optical and SEM images indicate that the thin film patterns were not perfect in terms of homogeneity, shape and geometry. However, the sample was considered to be well suited to be analyzed by LA-ICPMS. LA-ICPMS produced highly consistent images with sharp pattern boundaries. The rapid signal change from the thin film to background (or backwards) was considered as an indicator for high spatial resolution of about 1 µm. A scratch was introduced to the left arm of 'T' during sample transportation from one to the other laboratory and even this was imaged by LA-ICPMS in FIG. 9(c) and is consistent with the optical microscope image in FIG. 9(a) taken as a control picture.

Fast Imaging by Simultaneous Mattauch-Herzog Mass Spectrometer

A severe limitation of standard Quadrupole mass spectrometers is their sequential m/Q analyzing scheme. The short signal pulse duration resulting from the low dispersion tube cell limits the recording of multiple isotopes, unless quasi- or simultaneous mass spectrometers are coupled to LA-ICP. Examples of such advanced MS include Mattauch-Herzog MS (MH-MS) and Time-of-Flight-MS (TOF-MS). In order to illustrate the multi-element imaging capabilities of a MH-MS instrument, the same LA-ICP system as described for quadrupole ICPMS was coupled. The images obtained with this system were of similar quality and resolution as for quadrupole MS. It should be mentioned here that an LA-ICP-TOF-MS coupling would be equally suited for such rapid chemical imaging applications.

Tissue Imaging

Among the many possible applications of the presently disclosed elemental imaging LA-ICPMS system, it was decided to demonstrate its potential by investigating biomarker distributions in a biological tissue thin section. Such analyses demand, first, low m resolution to resolve the morphology of and to localize biomarkers within the smallest biological unit, the cell. This information is crucial in the study of biological processes and for comprehensive diagnostic purposes. Second, such analyses demand a short measurement time per pixel, as feasible using the presently disclosed ablation cell; in biological and biomedical analyses typically a large number of samples and large tissue areas (500×500 µm$^2$) need to be analyzed for statistical purposes. Therefore, a breast cancer tissue section was analyzed to investigate the human epidermal growth factor receptor 2 (HER2) statuses of individual cells illustrated in FIG. 6. The image showed HER2 protein highly expressed on the cell membrane. HER2 is a major determinant of relapse free survival time, time to metastasis and overall survival time after an initial breast cancer diagnosis. In the analysis, ~1 µm spatial resolution was achieved. Such high spatial resolution and chemical sensitivity allowed a highly precise HER2 determination in the breast cancer tissue. This sub-cellular resolution of an important biomarker for breast cancer analysis may be suitable to guide pathologists in their various treatment options.

It will be understood that the invention is described above by way of example only and modifications may be made whilst remaining within the scope and spirit of the invention.

[1] Pisonero et al. (2006) *J. Anal. At. Spectrom.* 21: 922-931
[2] Asogan et al. (2009), *J. Anal. At. Spectrom.* 24: 917-923
[3] Tanner et al. (2013) *Cancer Immunol Immunother* 62:955-965
[4] Hutchinson et al. (2005) *Anal. Biochem.* 346:225-33.
[5] Seuma et al. (2008) *Proteomics* 8:3775-84.
[6] Giesen et al. (2011) *Anal. Chem.* 83:8177-83.
[7] Giesen et al. (2014) *Nature Methods*. Published online Mar. 2, 2014—doi:10.1038/nmeth.2869
[8] Kindness et al. (2003) *Clin Chem* 49:1916-23.
[9] Gurevich & Hergenroder (2007) *J. Anal. At. Spectrom.*, 22:1043-1050.
[10] Wang et al. (2013) *Anal. Chem.* 85:10107-16.
[11] PCT/EP2013/056115.
[12] Herbert & Johnstone, *Mass Spectrometry Basics*, CRC Press 2002.
[13] Bandura et al. (2009) *Anal. Chem.*, 81:6813-22.
[14] Bendall et al. (2011) *Science* 332, 687-696.
[15] Bodenmiller et al. (2012) *Nat. Biotechnol.* 30:858-867.
[16] U.S. Pat. No. 7,479,630.
[17] Robichaud et al. (2013) *J Am Soc Mass Spectrom* 24(5):718-21.
[18] Klinkert et al. (2014) *Int J Mass Spectrom* http://dx.doi.org/10.1016/j.ijms.2013.12.012
[19] Qiu et al. (2011) *Nat. Biotechnol.* 29:886-91.
[20] Bruckner et al. (2013) *Anal. Chem.* 86:585-91.
[21] Gao & Yu (2007) *Biosensor Bioelectronics* 22:933-40.
[22] Duraiyan et al. (2012) *J Pharm Bioallied Sci.*, 4(Suppl 2): S307-S309.

What is claimed is:

1. A system comprising:
   a laser ablation cell top comprising a flow channel;
   wherein the flow channel extends from a gas inlet to a gas outlet;
   wherein the flow channel comprises a lateral opening and a lateral window;
   wherein the cell top is separate from a cell bottom that forms a sample chamber; and
   wherein the flow channel is adapted to couple to an inductively coupled plasma (ICP) torch.

2. The system of claim 1, wherein the cell top is removable from the cell bottom.

3. The system of claim 1, further comprising the cell bottom.

4. The system of claim 3, wherein the flow channel of the cell top and the sample chamber of the cell bottom are separated by a separating wall.

5. The system of claim 4, wherein the lateral opening is formed in the separating wall.

6. The system of claim 3, further comprising a laser adapted to shoot a laser beam through both the lateral window and the lateral opening of the ablation cell and impinge on the surface of a sample received by the sample chamber to generate a plume from the sample.

7. The system of claim 3, wherein the sample chamber comprises a positioning device.

8. The system of claim 1, further comprising the ICP torch coupled to the gas outlet of the flow channel.

9. The system of claim 8, further comprising a mass analyzer coupled to the ICP torch.

10. The system of claim 9, wherein the mass analyzer is a time-of-flight mass analyzer.

11. The system of claim 1, wherein the flow channel is a tube cell.

12. The system of claim 6, wherein the laser ablation cell is adapted to have a washout time of 100 ms or less.

* * * * *